US012636341B2

(12) United States Patent
Akahata

(10) Patent No.: US 12,636,341 B2
(45) Date of Patent: May 26, 2026

(54) GALECTIN-TARGETING IMMUNOTHERAPY

(71) Applicant: VLP Therapeutics, Inc., Wilmington, DE (US)

(72) Inventor: Wataru Akahata, Kensington, MD (US)

(73) Assignee: VLP Therapeutics, Inc., Wilmington, DE (US)

( * ) Notice: Subject to any disclaimer, the term of this patent is extended or adjusted under 35 U.S.C. 154(b) by 987 days.

(21) Appl. No.: 17/726,623

(22) Filed: Apr. 22, 2022

(65) Prior Publication Data

US 2022/0347261 A1    Nov. 3, 2022

Related U.S. Application Data

(60) Provisional application No. 63/178,755, filed on Apr. 23, 2021.

(51) Int. Cl.
| | |
|---|---|
| *C12N 15/70* | (2006.01) |
| *A61K 38/16* | (2006.01) |
| *A61K 39/00* | (2006.01) |
| *C07K 16/10* | (2006.01) |

(52) U.S. Cl.
CPC .... *A61K 38/162* (2013.01); *A61K 39/001166* (2018.08); *C07K 16/10* (2013.01); *C12N 15/70* (2013.01); *A61K 2039/505* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 6,753,314 | B1 * | 6/2004 | Giot ..................... | C07K 14/395 |
| | | | | 435/7.1 |
| 9,249,191 | B2 | 2/2016 | Ueno et al. | |
| 9,353,353 | B2 * | 5/2016 | Nabel ..................... | A61P 31/12 |
| 9,487,563 | B2 | 11/2016 | Nabel et al. | |
| 9,969,986 | B2 | 5/2018 | Akahata et al. | |
| 11,407,797 | B2 * | 8/2022 | Hudalla, II .............. | A61P 19/02 |
| 2004/0023855 | A1 | 2/2004 | John et al. | |
| 2005/0118191 | A1 | 6/2005 | Robinson et al. | |
| 2014/0363458 | A1 | 12/2014 | Ueno et al. | |

FOREIGN PATENT DOCUMENTS

| | | | |
|---|---|---|---|
| JP | 2016-521539 | A | 7/2016 |
| JP | 2021-501180 | A | 1/2021 |
| WO | 2016/021209 | A1 | 2/2016 |
| WO | 2017/009400 | A1 | 1/2017 |
| WO | 2017/074235 | A1 | 5/2017 |
| WO | 2018/029586 | A1 | 2/2018 |
| WO | 2018/138257 | A1 | 8/2018 |
| WO | 2019/089080 | A9 | 5/2019 |
| WO | 2024/143497 | A1 | 7/2024 |

OTHER PUBLICATIONS

Yang et al. (Journal of Virology, 2011, p. 10010-10020).*
Communication, dated Jul. 12, 2022, issued by the International Searching Authority in International application No. PCT/JP2022/018610.
Yazar et al., "A preliminary data: Evaluation of serum Galectin-3 levels in patients with Idiopathic Parkinson's Disease", Journal of Clinical Neuroscience, 2019, vol. 70, pp. 164-168.
Boza-Serrano et al., "Galectin-3, a novel endogenous TREM2 ligand, detrimentally regulates inflammatory response in Alzheimer's disease", Acta Neuropathologica, 2019, vol. 138, pp. 251-273.
Ashraf et al., "Investigation of Gal-3 Expression Pattern in Serum and Cerebrospinal Fluid of Patients Suffering From Neurodegenerative Disorders", Frontiers in Neuroscience, Jun. 29, 2018, vol. 12, Article 430, pp. 1-8.
Roldão et al., "Virus-like particles in vaccine development", Expert Rev. Vaccines, 2010, vol. 9, No. 10, pp. 1149-1176.
Goldfarb et al., "Pathways for the nuclear transport of proteins and RNAs", Trends in Cell Biology, Jul. 1991, vol. 1, pp. 20-24.
Görlich et al., "Nucleocytoplasmic Transport", Science, Mar. 15, 1996, vol. 271, pp. 1513-1518.
Schneider et al., "A Mutant SV40 Large T Antigen Interferes with Nuclear Localization of a Heterologous Protein", Cell, 1988, vol. 54, pp. 117-125.
Dingwall et al., "The Nucleoplasmin Nuclear Location Sequence Is Larger and More Complex than That of SV-40 Large T Antigen", The Journal of Cell Biology, Sep. 1988, vol. 107, pp. 841-849.
Hirani et al., "Target inhibition of galectin-3 by inhaled TD139 in patients with idiopathic pulmonary fibrosis", Eur Respir J, Interstitial Lung Disease, 2021, vol. 57, pp. 1-13.
International Search Report dated Jun. 20, 2023, issued in International Application No. PCT/JP2023/015132.
Goto et al., "A development of novel vaccine targeting galectin-3 for Alzheimer's disease", Clinical Neurology [online], 2021, vol. 61, Supplement, p. S223 Abstract No. AP-01-5 (1 page).
Goto, K. et al., Development of novel vaccine to reduce galectin-3 for Alzheimer's disease, Journal of the Neurological Sciences, 2021, vol. 429, Abstracts, pp. 108-109, Article No. 119028.
Barondes SH, et al., "Galectins. Structure and function of a large family of animal lectins", The Journal of Biological Chemistry, vol. 269, No. 33, pp. 20807-20810, Aug. 19, 1994 (4 pages total).
Astorgues-Xerri L, et al., "Unraveling galectin-1 as a novel therapeutic target for cancer", Cancer Treatment Reviews, vol. 40, pp. 307-319, 2014 (13 pages total).
Banh A, et al., "Tumor galectin-1 mediates tumor growth and metastasis through regulation of T-cell apoptosis" Cancer Res, vol. 71, No. 13, 2011, pp. 4423-4431(15 pages total).
Salatino, Mariana, et al., "Regulation of Galectins by Hypoxia and Their Relevance in Angiogenesis: Strategies and Methods", Methods in Molecular Biology Galectins, 2014, pp. 293-304 (12 pages total).

(Continued)

*Primary Examiner* — Agnieszka Boesen
(74) *Attorney, Agent, or Firm* — Sughrue Mion, PLLC

(57) ABSTRACT

The present disclosure provides a virus like particle comprising a viral structural protein and a galectin epitope peptide, and a composition or vaccine comprising thereof, its use in a medicine, particularly in an immunotherapy.

15 Claims, 16 Drawing Sheets

Specification includes a Sequence Listing.

(56) References Cited

OTHER PUBLICATIONS

Xu-Yun Zhao, et al., "Hypoxia inducible factor-1 mediates expression of galectin-1: the potential role in migration/invasion of colorectal cancer cells", Carcinogenesis, vol. 31, No. 8, 2010, pp. 1367-1375 (9 pages total).

Thijssen, V.L.J.L., et al., "Galectin-1 is essential in tumor angiogenesis and is a target for antiangiogenesis therapy", Proc Natl Acad Sci, vol. 103, No. 43, 2006, pp. 15975-15980 (6 pages total).

Koonce N.A., et al., "Galectin-1 Inhibitor OTX008 Induces Tumor Vessel Normalization and Tumor Growth Inhibition in Human Head and Neck Squamous Cell Carcinoma Models", International Journal of Molecular Science, vol. 18, No. 2671, 2017, pp. 1-9 (9 pages total).

Diego O. Croci, et al., "Disrupting galectin-1 interactions with N-glycans suppresses hypoxia-driven angiogenesis and tumorigenesis in Kaposi's sarcoma", J. Exp. Med., vol. 209, No. 11, 2012, pp. 1985-2000 (16 pages total).

Van der Schaft D.W., et al., "The designer anti-angiogenic peptide anginex targets tumor endothelial cells and inhibits tumor growth in animal models." FASEB J., vol. 16, No. 14, 2002 (1 page total).

Henderson N.C., et al., "Galectin-3 regulates myofibroblast activation and hepatic fibrosis", Proc Natl Acad Sci, vol. 103, No. 13, Mar. 28, 2006, pp. 5060-5065 (6 pages total).

Mourad-Zeidan A.A., et al., "Expression profiling of Galectin-3-depleted melanoma cells reveals its major role in melanoma cell plasticity and vasculogenic mimicry", Am J Pathol, vol. 173, No. 6, Dec. 2008, pp. 1839-1852 (14 pages total).

Reynolds, H.Y., "Lung inflammation and fibrosis: an alveolar macrophage-centered perspective from the 1970s to 1980s", Am J Respir Crit Care Med, vol. 171, 2005, pp. 98-102 (5 pages total).

MacKinnon A.C et al., "Regulation of alternative macrophage activation by galectin-3", J Immunol, vol. 180, 2008, pp. 2650-2658 (10 pages total).

Dumic J, et al., "Galectin-3: An open-ended story", Biochimica et Biophysica Acta, vol. 1760, 2006, pp. 616-635 (20 pages total).

Kuklinski S, et al., "Homophilic binding properties of galectin-3: Involvement of the carbohydrate recognition domain", J Neurochem, vol. 70, 1998, pp. 814-823 (10 pages total).

Lepur A, et al., "Ligand induced galectin-3 protein self-association", J Biol Chem, vol. 287, No. 26, Jun. 22, 2012, pp. 21751-21756 (6 pages total).

Yang RY, et al., "Expression of galectin-3 modulates T-cell growth and apoptosis", Proc Natl Acad Sci, vol. 93, Jun. 1996, pp. 6737-6742 (6 pages total).

Henderson N. C., et al., "Galectin-3 expression and secretion links macrophages to the promotion of renal fibrosis", Am J Pathol., vol. 172, No. 2, Feb. 2008, pp. 288-298 (11 pages total).

Barman, Scott A, et al., "Galectin-3 is Expressed in Vascular Smooth Muscle Cells and Promotes Pulmonary Hypertension through changes in Proliferation, Apoptosis and Fibrosis." Am J Physiol Lung Cell Mol Physiol., vol. 316, pp. L784-L797, Feb. 6, 2019 (14 pages total).

Nishi Y, et al., "Role of Galectin-3 in Human Pulmonary Fibrosis", Allergol Int., vol. 56, No. 1, 2007, pp. 57-65 (9 pages total).

De Boer, R. A., et al., "Galectin-3 in cardiac remodeling and heart failure", Curr. Heart Fail. Rep., vol. 7, 2010, pp. 1-8 (8 pages total).

Nikhil Hirani, et al., "TD139, A Novel Inhaled Galectin-3 Inhibitor for the Treatment of Idiopathic Pulmonary Fibrosis (IPF). Results from the First in (IPF) Patients Study." American Journal of Respiratory and Critical Care Medicine, vol. 195, A7560, 2017 (1 page total).

Yu L, et al., "Genetic and pharmacological inhibition of galectin-3 prevents cardiac remodeling by interfering with myocardial fibrogenesis", Circ Heart Fail, No. 6, Jan. 2013, pp. 107-117 (11 pages total).

Hellman, L., "Therapeutic vaccines against IgE-mediated allergies", Expert Rev. Vaccines, vol. 7, No. 2, 2008, pp. 193-208 (17 pages total).

Falk Saupe, et al., "Vaccines targeting self-antigens: mechanisms and efficacy-determining parameters", FASEB Journal, vo. 29, No. 8, 2005, pp. 3253-3262 (10 pages total).

Ko et al., "A virus-like particle vaccine prevents equine encephalitis virus infection in nonhuman primates", Science Translational Medicine, vol. 11, Article No. eaav3113, May 15, 2019, pp. 1-12.

Jodie Stephenson et al.; "Inflammation in CNS neurodegenerative diseases"; Immunology; vol. 154; 2018; pp. 204-219.

* cited by examiner

1: molecular marker
2: Control VLP
3: Gal-1 #5 VLP
4: Gal-1 #7 VLP
5: Gal-1 #12 VLP
6: Gal-1 #14 VLP Antibody Against
Human Gal1

Antibody Against
Mouse Gal1

Figure 3F

SEQUENCE LISTING

<160> NUMBER OF SEQ ID NOS: 24

<210> SEQ ID NO 1
<211> LENGTH: 1248
<212> TYPE: PRT
<213> ORGANISM: Chikungunya virus

<400> SEQUENCE: 1

-continued

```
Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
    275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
            325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
            405                 410                 415

Thr Ile Thr Gly Thr Met Gly His Phe Ile Leu Ala Arg Cys Pro Lys
```

-continued

```
                420                425                430

Gly Glu Thr Leu Thr Val Gly Phe Thr Asp Ser Arg Lys Ile Ser His
        435                440                445

Ser Cys Thr His Pro Phe His His Asp Pro Val Ile Gly Arg Glu
        450                455                460

Lys Phe His Ser Arg Pro Gln His Gly Lys Glu Leu Pro Cys Ser Thr
465                470                475                480

Tyr Val Gln Ser Thr Ala Ala Thr Thr Glu Glu Ile Glu Val His Met
                485                490                495

Pro Pro Asp Thr Pro Asp Arg Thr Leu Met Ser Gln Gln Ser Gly Asn
                500                505                510

Val Lys Ile Thr Val Asn Gly Gln Thr Val Arg Tyr Lys Cys Asn Cys
                515                520                525

Gly Gly Ser Asn Glu Gly Leu Thr Thr Thr Asp Lys Val Ile Asn Asn
        530                535                540

Cys Lys Val Asp Gln Cys His Ala Ala Val Thr Asn His Lys Lys Trp
545                550                555                560

Gln Tyr Asn Ser Pro Leu Val Pro Arg Asn Ala Glu Leu Gly Asp Arg
                565                570                575

Lys Gly Lys Ile His Ile Pro Phe Pro Leu Ala Asn Val Thr Cys Arg
                580                585                590

Val Pro Lys Ala Arg Asn Pro Thr Val Thr Tyr Gly Lys Asn Gln Val
                595                600                605

Ile Met Leu Leu Tyr Pro Asp His Pro Thr Leu Leu Ser Tyr Arg Asn
        610                615                620

Met Gly Glu Glu Pro Asn Tyr Gln Glu Glu Trp Val Met His Lys Lys
625                630                635                640

Glu Val Val Leu Thr Val Pro Thr Glu Gly Leu Glu Val Thr Trp Gly
                645                650                655

Asn Asn Glu Pro Tyr Lys Tyr Trp Pro Gln Leu Ser Thr Asn Gly Thr
                660                665                670

Ala His Gly His Pro His Glu Ile Ile Leu Tyr Tyr Tyr Glu Leu Tyr
        675                680                685

Pro Thr Met Thr Val Val Val Val Ser Val Ala Thr Phe Ile Leu Leu
        690                695                700

Ser Met Val Gly Met Ala Ala Gly Met Cys Met Cys Ala Arg Arg Arg
705                710                715                720

Cys Ile Thr Pro Tyr Glu Leu Thr Pro Gly Ala Thr Val Pro Phe Leu
                725                730                735

Leu Ser Leu Ile Cys Cys Ile Arg Thr Ala Lys Ala Ala Thr Tyr Gln
        740                745                750

Glu Ala Ala Ile Tyr Leu Trp Asn Glu Gln Gln Pro Leu Phe Trp Leu
        755                760                765

Gln Ala Leu Ile Pro Leu Ala Ala Leu Ile Val Leu Cys Asn Cys Leu
        770                775                780

Arg Leu Leu Pro Cys Cys Cys Lys Thr Leu Ala Phe Leu Ala Val Met
785                790                795                800

Ser Val Gly Ala His Thr Val Ser Ala Tyr Glu His Val Thr Val Ile
                805                810                815

Pro Asn Thr Val Gly Val Pro Tyr Lys Thr Leu Val Asn Arg Pro Gly
                820                825                830

Tyr Ser Pro Met Val Leu Glu Met Glu Leu Leu Ser Val Thr Leu Glu
        835                840                845
```

-continued

```
Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
                915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
                980                 985                 990

Val Tyr Asn Met Asp Tyr Pro Pro  Phe Gly Ala Gly Arg  Pro Gly Gln
    995                 1000                1005

Phe Gly  Asp Ile Gln Ser Arg  Thr Pro Glu Ser Lys  Asp Val Tyr
    1010                1015                1020

Ala Asn  Thr Gln Leu Val Leu  Gln Arg Pro Ala Val  Gly Thr Val
    1025                1030                1035

His Val  Pro Tyr Ser Gln Ala  Pro Ser Gly Phe Lys  Tyr Trp Leu
    1040                1045                1050

Lys Glu  Arg Gly Ala Ser Leu  Gln His Thr Ala Pro  Phe Gly Cys
    1055                1060                1065

Gln Ile  Ala Thr Asn Pro Val  Arg Ala Val Asn Cys  Ala Val Gly
    1070                1075                1080

Asn Met  Pro Ile Ser Ile Asp  Ile Pro Glu Ala Ala  Phe Thr Arg
    1085                1090                1095

Val Val  Asp Ala Pro Ser Leu  Thr Asp Met Ser Cys  Glu Val Pro
    1100                1105                1110

Ala Cys  Thr His Ser Ser Asp  Phe Gly Gly Val Ala  Ile Ile Lys
    1115                1120                1125

Tyr Ala  Ala Ser Lys Lys Gly  Lys Cys Ala Val His  Ser Met Thr
    1130                1135                1140

Asn Ala  Val Thr Ile Arg Glu  Ala Glu Ile Glu Val  Glu Gly Asn
    1145                1150                1155

Ser Gln  Leu Gln Ile Ser Phe  Ser Thr Ala Leu Ala  Ser Ala Glu
    1160                1165                1170

Phe Arg  Val Gln Val Cys Ser  Thr Gln Val His Cys  Ala Ala Glu
    1175                1180                1185

Cys His  Pro Pro Lys Asp His  Ile Val Asn Tyr Pro  Ala Ser His
    1190                1195                1200

Thr Thr  Leu Gly Val Gln Asp  Ile Ser Ala Thr Ala  Met Ser Trp
    1205                1210                1215

Val Gln  Lys Ile Thr Gly Gly  Val Gly Leu Val Val  Ala Val Ala
    1220                1225                1230

Ala Leu  Ile Leu Ile Val Val  Leu Cys Val Ser Phe  Ser Arg His
    1235                1240                1245
```

```
<210> SEQ ID NO 2
<211> LENGTH: 1248
<212> TYPE: PRT
<213> ORGANISM: Chikungunya virus

<400> SEQUENCE: 2

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
            115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
            275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
            325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
    370                 375                 380
```

```
Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
                420                 425                 430

Gly Glu Thr Leu Thr Val Gly Phe Thr Asp Ser Arg Lys Ile Ser His
                435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
                500                 505                 510

Val Lys Ile Thr Val Asn Gly Gln Thr Val Arg Tyr Lys Cys Asn Cys
                515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
                580                 585                 590

Val Pro Lys Ala Arg Asn Pro Thr Val Thr Tyr Gly Lys Asn Gln Val
                595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
                660                 665                 670

Ala His Gly His Pro His Glu Ile Ile Leu Tyr Tyr Tyr Glu Leu Tyr
                675                 680                 685

Pro Thr Met Thr Val Val Ile Val Ser Val Ala Ser Phe Val Leu Leu
    690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
                740                 745                 750

Glu Ala Ala Ala Tyr Leu Trp Asn Glu Gln Gln Pro Leu Phe Trp Leu
                755                 760                 765

Gln Ala Leu Ile Pro Leu Ala Ala Leu Ile Val Leu Cys Asn Cys Leu
    770                 775                 780

Lys Leu Leu Pro Cys Cys Cys Lys Thr Leu Ala Phe Leu Ala Val Met
785                 790                 795                 800
```

-continued

```
Ser Ile Gly Ala His Thr Val Ser Ala Tyr Glu His Val Thr Val Ile
            805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
            835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
            885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
            930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
            965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
            995                 1000                1005

Phe Gly  Asp Ile Gln Ser Arg  Thr Pro Glu Ser Lys  Asp Val Tyr
    1010                 1015                1020

Ala Asn  Thr Gln Leu Val Leu  Gln Arg Pro Ala Ala  Gly Thr Val
    1025                 1030                1035

His Val  Pro Tyr Ser Gln Ala  Pro Ser Gly Phe Lys  Tyr Trp Leu
    1040                 1045                1050

Lys Glu  Arg Gly Ala Ser Leu  Gln His Thr Ala Pro  Phe Gly Cys
    1055                 1060                1065

Gln Ile  Ala Thr Asn Pro Val  Arg Ala Val Asn Cys  Ala Val Gly
    1070                 1075                1080

Asn Ile  Pro Ile Ser Ile Asp  Ile Pro Asp Ala Ala  Phe Thr Arg
    1085                 1090                1095

Val Val  Asp Ala Pro Ser Val  Thr Asp Met Ser Cys  Glu Val Pro
    1100                 1105                1110

Ala Cys  Thr His Ser Ser Asp  Phe Gly Gly Val Ala  Ile Ile Lys
    1115                 1120                1125

Tyr Thr  Ala Ser Lys Lys Gly  Lys Cys Ala Val His  Ser Met Thr
    1130                 1135                1140

Asn Ala  Val Thr Ile Arg Glu  Ala Asp Val Glu Val  Glu Gly Asn
    1145                 1150                1155

Ser Gln  Leu Gln Ile Ser Phe  Ser Thr Ala Leu Ala  Ser Ala Glu
    1160                 1165                1170

Phe Arg  Val Gln Val Cys Ser  Thr Gln Val His Cys  Ala Ala Ala
    1175                 1180                1185

Cys His  Pro Pro Lys Asp His  Ile Val Asn Tyr Pro  Ala Ser His
    1190                 1195                1200

Thr Thr  Leu Gly Val Gln Asp  Ile Ser Thr Thr Ala  Met Ser Trp
```

-continued

```
        1205                1210                1215

Val Gln Lys Ile Thr Gly Gly  Val Gly Leu Ile Val  Ala Val Ala
    1220                1225                1230

Ala Leu  Ile Leu Ile Val Val  Leu Cys Val Ser Phe  Ser Arg His
    1235                1240                1245

<210> SEQ ID NO 3
<211> LENGTH: 1255
<212> TYPE: PRT
<213> ORGANISM: Venezuelan equine encephalitis virus

<400> SEQUENCE: 3

Met Phe Pro Phe Gln Pro Met Tyr Pro Met Gln Pro Met Pro Tyr Arg
1                 5                   10                  15

Asn Pro Phe Ala Ala Pro Arg Arg Pro Trp Phe Pro Arg Thr Asp Pro
                20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
                100                 105                 110

Gly Lys Arg Gln Arg Met Val Met Lys Leu Glu Ser Asp Lys Thr Phe
                115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
                180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
                260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335
```

-continued

```
Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu
        355                 360                 365

Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
            405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
            485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
            515                 520                 525

Ser Ala Leu Val Glu Cys Glu Cys Gly Gly Thr Lys Ile Ser Glu Thr
    530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
            565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
            595                 600                 605

Met Ile Thr Phe Gly Phe Arg Ser Val Ser Leu Lys Leu His Pro Lys
    610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
            645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
            675                 680                 685

Val Ile Thr His Tyr Tyr His Arg Tyr Pro Met Ser Thr Ile Leu Gly
            690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
```

-continued

```
              755               760               765
Asn Asn Asn Gln Gln Met Phe Trp Ile Gln Leu Leu Ile Pro Leu Ala
    770               775               780
Ala Leu Ile Val Val Thr Arg Leu Leu Arg Cys Val Cys Cys Val Val
785               790               795               800
Pro Phe Leu Val Met Ala Gly Ala Ala Gly Ala Gly Ala Tyr Glu His
                805               810               815
Ala Thr Thr Met Pro Ser Gln Ala Gly Ile Ser Tyr Asn Thr Ile Val
                820               825               830
Asn Arg Ala Gly Tyr Ala Pro Leu Pro Ile Ser Ile Thr Pro Thr Lys
        835               840               845
Ile Lys Leu Ile Pro Thr Val Asn Leu Glu Tyr Val Thr Cys His Tyr
    850               855               860
Lys Thr Gly Met Asp Ser Pro Ala Ile Lys Cys Cys Gly Ser Gln Glu
865               870               875               880
Cys Thr Pro Thr Tyr Arg Pro Asp Glu Gln Cys Lys Val Phe Thr Gly
                885               890               895
Val Tyr Pro Phe Met Trp Gly Gly Ala Tyr Cys Phe Cys Asp Thr Glu
                900               905               910
Asn Thr Gln Val Ser Lys Ala Tyr Val Met Lys Ser Asp Asp Cys Leu
    915               920               925
Ala Asp His Ala Glu Ala Tyr Lys Ala His Thr Ala Ser Val Gln Ala
    930               935               940
Phe Leu Asn Ile Thr Val Gly Glu His Ser Ile Val Thr Thr Val Tyr
945               950               955               960
Val Asn Gly Glu Thr Pro Val Asn Phe Asn Gly Val Lys Ile Thr Ala
                965               970               975
Gly Pro Leu Ser Thr Ala Trp Thr Pro Phe Asp Arg Lys Ile Val Gln
        980               985               990
Tyr Ala Gly Glu Ile Tyr Asn Tyr  Asp Phe Pro Glu Tyr  Gly Ala Gly
        995               1000               1005
Gln Pro  Gly Ala Phe Gly Asp  Ile Gln Ser Arg Thr  Val Ser Ser
    1010               1015               1020
Ser Asp  Leu Tyr Ala Asn Thr  Asn Leu Val Leu Gln  Arg Pro Lys
    1025               1030               1035
Ala Gly  Ala Ile His Val Pro  Tyr Thr Gln Ala Pro  Ser Gly Phe
    1040               1045               1050
Glu Gln  Trp Lys Lys Asp Lys  Ala Pro Ser Leu Lys  Phe Thr Ala
    1055               1060               1065
Pro Phe  Gly Cys Glu Ile Tyr  Thr Asn Pro Ile Arg  Ala Glu Asn
    1070               1075               1080
Cys Ala  Val Gly Ser Ile Pro  Leu Ala Phe Asp Ile  Pro Asp Ala
    1085               1090               1095
Leu Phe  Thr Arg Val Ser Glu  Thr Pro Thr Leu Ser  Ala Ala Glu
    1100               1105               1110
Cys Thr  Leu Asn Glu Cys Val  Tyr Ser Ser Asp Phe  Gly Gly Ile
    1115               1120               1125
Ala Thr  Val Lys Tyr Ser Ala  Ser Lys Ser Gly Lys  Cys Ala Val
    1130               1135               1140
His Val  Pro Ser Gly Thr Ala  Thr Leu Lys Glu Ala  Ala Val Glu
    1145               1150               1155
Leu Thr  Glu Gln Gly Ser Ala  Thr Ile His Phe Ser  Thr Ala Asn
    1160               1165               1170
```

-continued

```
Ile His  Pro Glu Phe Arg Leu  Gln Ile Cys Thr Ser  Tyr Val Thr
    1175              1180              1185

Cys Lys  Gly Asp Cys His Pro  Pro Lys Asp His Ile  Val Thr His
    1190              1195              1200

Pro Gln  Tyr His Ala Gln Thr  Phe Thr Ala Ala Val  Ser Lys Thr
    1205              1210              1215

Ala Trp  Thr Trp Leu Thr Ser  Leu Leu Gly Gly Ser  Ala Val Ile
    1220              1225              1230

Ile Ile  Ile Gly Leu Val Leu  Ala Thr Ile Val Ala  Met Tyr Val
    1235              1240              1245

Leu Thr  Asn Gln Lys His Asn
    1250              1255

<210> SEQ ID NO 4
<211> LENGTH: 61
<212> TYPE: PRT
<213> ORGANISM: Chikungunya virus

<400> SEQUENCE: 4

Ala Thr Tyr Gln Glu Ala Ala Ile Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Arg Leu Leu Pro Cys Cys Cys Lys Thr Leu Ala Phe
        35                  40                  45

Leu Ala Val Met Ser Val Gly Ala His Thr Val Ser Ala
    50                  55                  60

<210> SEQ ID NO 5
<211> LENGTH: 61
<212> TYPE: PRT
<213> ORGANISM: Chikungunya virus

<400> SEQUENCE: 5

Ala Thr Tyr Tyr Glu Ala Ala Ala Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Lys Leu Leu Pro Cys Cys Cys Lys Thr Leu Ala Phe
        35                  40                  45

Leu Ala Val Met Ser Ile Gly Ala His Thr Val Ser Ala
    50                  55                  60

<210> SEQ ID NO 6
<211> LENGTH: 56
<212> TYPE: PRT
<213> ORGANISM: Venezuelan equine encephalitis virus

<400> SEQUENCE: 6

Glu Thr Thr Trp Glu Ser Leu Asp His Leu Trp Asn Asn Asn Gln Gln
1               5                   10                  15

Met Phe Trp Ile Gln Leu Leu Ile Pro Leu Ala Ala Leu Ile Val Val
            20                  25                  30

Thr Arg Leu Leu Arg Cys Val Cys Cys Val Val Pro Phe Leu Val Met
        35                  40                  45

Ala Gly Ala Ala Gly Ala Gly Ala
    50                  55
```

-continued

<210> SEQ ID NO 7
<211> LENGTH: 135
<212> TYPE: PRT
<213> ORGANISM: homo sapiens

<400> SEQUENCE: 7

```
Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135
```

<210> SEQ ID NO 8
<211> LENGTH: 250
<212> TYPE: PRT
<213> ORGANISM: homo sapiens

<400> SEQUENCE: 8

```
Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190
```

-continued

```
Glu Ser Gly Lys Pro Phe Lys Ile Gln Val Leu Val Glu Pro Asp His
        195             200             205

Phe Lys Val Ala Val Asn Asp Ala His Leu Leu Gln Tyr Asn His Arg
        210             215             220

Val Lys Lys Leu Asn Glu Ile Ser Lys Leu Gly Ile Ser Gly Asp Ile
225             230             235             240

Asp Leu Thr Ser Ala Ser Tyr Thr Met Ile
                245             250

<210> SEQ ID NO 9
<211> LENGTH: 55
<212> TYPE: PRT
<213> ORGANISM: Homo sapiens

<400> SEQUENCE: 9

Ser Phe Val Leu Asn Leu Gly Lys Asp Ser Asn Asn Leu Ser Leu His
1               5               10              15

Phe Asn Pro Arg Phe Asn Ala His Gly Asp Ala Asn Thr Ile Val Ser
                20              25              30

Asn Ser Lys Asp Gly Gly Ala Trp Gly Thr Glu Gln Arg Glu Ala Val
        35              40              45

Phe Pro Phe Gln Pro Gly Ser
        50              55

<210> SEQ ID NO 10
<211> LENGTH: 23
<212> TYPE: PRT
<213> ORGANISM: homo sapiens

<400> SEQUENCE: 10

Ala Asn Leu Thr Val Lys Leu Pro Asp Gly Tyr Glu Phe Lys Phe Pro
1               5               10              15

Asn Arg Leu Asn Leu Glu Ala
                20

<210> SEQ ID NO 11
<211> LENGTH: 55
<212> TYPE: PRT
<213> ORGANISM: Mus musculus

<400> SEQUENCE: 11

Ser Phe Val Leu Asn Leu Gly Lys Asp Ser Asn Asn Leu Ser Leu His
1               5               10              15

Phe Asn Pro Arg Phe Asn Ala His Gly Asp Ala Asn Thr Ile Val Ser
                20              25              30

Asn Thr Lys Glu Asp Gly Thr Trp Gly Thr Glu His Arg Glu Pro Ala
        35              40              45

Phe Pro Phe Gln Pro Gly Ser
        50              55

<210> SEQ ID NO 12
<211> LENGTH: 23
<212> TYPE: PRT
<213> ORGANISM: Mus musculus

<400> SEQUENCE: 12

Ala Asp Leu Thr Ile Lys Leu Pro Asp Gly His Glu Phe Lys Phe Pro
1               5               10              15

Asn Arg Leu Asn Met Glu Ala
                20
```

```
<210> SEQ ID NO 13
<211> LENGTH: 30
<212> TYPE: PRT
<213> ORGANISM: homo sapiens

<400> SEQUENCE: 13

Ala Asp Asn Phe Ser Leu His Asp Ala Leu Ser Gly Ser Gly Asn Pro
1               5                   10                  15

Asn Pro Gln Gly Trp Pro Gly Ala Trp Gly Asn Gln Pro Ala
            20                  25                  30

<210> SEQ ID NO 14
<211> LENGTH: 34
<212> TYPE: PRT
<213> ORGANISM: homo sapiens

<400> SEQUENCE: 14

Tyr Pro Gly Ala Ser Tyr Pro Gly Ala Tyr Pro Gly Gln Ala Pro Pro
1               5                   10                  15

Gly Ala Tyr Pro Gly Gln Ala Pro Pro Gly Ala Tyr Pro Gly Ala Pro
            20                  25                  30

Gly Ala

<210> SEQ ID NO 15
<211> LENGTH: 74
<212> TYPE: PRT
<213> ORGANISM: homo sapiens

<400> SEQUENCE: 15

Tyr Pro Gly Ala Ser Tyr Pro Gly Ala Tyr Pro Gly Gln Ala Pro Pro
1               5                   10                  15

Gly Ala Tyr Pro Gly Gln Ala Pro Pro Gly Ala Tyr Pro Gly Ala Pro
            20                  25                  30

Gly Ala Tyr Pro Gly Ala Pro Ala Pro Gly Val Tyr Pro Gly Pro Pro
        35                  40                      45

Ser Gly Pro Gly Ala Tyr Pro Ser Ser Gly Gln Pro Ser Ala Thr Gly
    50                  55                  60

Ala Tyr Pro Ala Thr Gly Pro Tyr Gly Ala
65                  70

<210> SEQ ID NO 16
<211> LENGTH: 30
<212> TYPE: PRT
<213> ORGANISM: Mus musculus

<400> SEQUENCE: 16

Ala Asp Ser Phe Ser Leu Asn Asp Ala Leu Ala Gly Ser Gly Asn Pro
1               5                   10                  15

Asn Pro Gln Gly Tyr Pro Gly Ala Trp Gly Asn Gln Pro Gly
            20                  25                  30

<210> SEQ ID NO 17
<211> LENGTH: 27
<212> TYPE: PRT
<213> ORGANISM: Homo sapiens

<400> SEQUENCE: 17

Asn Asn Leu Ser Leu His Phe Asn Pro Arg Phe Asn Ala His Gly Asp
1               5                   10                  15
```

```
Ala Asn Thr Ile Val Ser Asn Ser Lys Asp Gly
            20                  25

<210> SEQ ID NO 18
<211> LENGTH: 17
<212> TYPE: PRT
<213> ORGANISM: Homo sapiens

<400> SEQUENCE: 18

Ala Asn Leu Thr Val Lys Leu Pro Asp Gly Tyr Glu Phe Lys Phe Pro
1               5                   10                  15

Asn

<210> SEQ ID NO 19
<211> LENGTH: 24
<212> TYPE: PRT
<213> ORGANISM: Homo sapiens

<400> SEQUENCE: 19

Gln Pro Gly Ser Val Ala Glu Val Ser Ile Thr Phe Asp Gln Ala Asn
1               5                   10                  15

Leu Thr Val Lys Leu Pro Asp Gly
            20

<210> SEQ ID NO 20
<211> LENGTH: 23
<212> TYPE: PRT
<213> ORGANISM: Homo sapiens

<400> SEQUENCE: 20

Ala Asn Thr Ile Val Ser Asn Ser Lys Asp Gly Gly Ala Trp Gly Thr
1               5                   10                  15

Glu Gln Arg Glu Ala Val Phe
            20

<210> SEQ ID NO 21
<211> LENGTH: 61
<212> TYPE: PRT
<213> ORGANISM: Artificial Sequence
<220> FEATURE:
<223> OTHER INFORMATION: Synthetic sequence

<400> SEQUENCE: 21

Ser Gly Gly Ser Phe Val Leu Asn Leu Gly Lys Asp Ser Asn Asn Leu
1               5                   10                  15

Ser Leu His Phe Asn Pro Arg Phe Asn Ala His Gly Asp Ala Asn Thr
            20                  25                  30

Ile Val Ser Asn Ser Lys Asp Gly Gly Ala Trp Gly Thr Glu Gln Arg
            35                  40                  45

Glu Ala Val Phe Pro Phe Gln Pro Gly Ser Gly Gly Ser
        50                  55                  60

<210> SEQ ID NO 22
<211> LENGTH: 29
<212> TYPE: PRT
<213> ORGANISM: Artificial Sequence
<220> FEATURE:
<223> OTHER INFORMATION: Synthetic sequence

<400> SEQUENCE: 22

Ser Gly Gly Ala Asn Leu Thr Val Lys Leu Pro Asp Gly Tyr Glu Phe
1               5                   10                  15
```

-continued

```
Lys Phe Pro Asn Arg Leu Asn Leu Glu Ala Gly Gly Ser
            20                  25

<210> SEQ ID NO 23
<211> LENGTH: 61
<212> TYPE: PRT
<213> ORGANISM: Artificial Sequence
<220> FEATURE:
<223> OTHER INFORMATION: Synthetic sequence

<400> SEQUENCE: 23

Ser Gly Gly Ser Phe Val Leu Asn Leu Gly Lys Asp Ser Asn Asn Leu
1               5                   10                  15

Ser Leu His Phe Asn Pro Arg Phe Asn Ala His Gly Asp Ala Asn Thr
            20                  25                  30

Ile Val Ser Asn Thr Lys Glu Asp Gly Thr Trp Gly Thr Glu His Arg
        35                  40                  45

Glu Pro Ala Phe Pro Phe Gln Pro Gly Ser Gly Gly Ser
    50                  55                  60

<210> SEQ ID NO 24
<211> LENGTH: 29
<212> TYPE: PRT
<213> ORGANISM: Artificial Sequence
<220> FEATURE:
<223> OTHER INFORMATION: Synthetic sequence

<400> SEQUENCE: 24

Ser Gly Gly Ala Asp Leu Thr Ile Lys Leu Pro Asp Gly His Glu Phe
1               5                   10                  15

Lys Phe Pro Asn Arg Leu Asn Met Glu Ala Gly Gly Ser
            20                  25
```

GALECTIN-TARGETING IMMUNOTHERAPY

CROSS REFERENCE TO RELATED APPLICATIONS

This application claims the benefit of U.S. Provisional Patent Application No. 63/178,755 filed on Apr. 23, 2021. The entire disclosure of this prior application is hereby incorporated by reference.

INCORPORATION BY REFERENCE OF SEQUENCE LISTING

The content of the electronically submitted sequence listing, file name: Q273666_Substitute Sequence Listing.txt; size: 44,268 bytes; and date of creation: Dec. 14, 2025, filed herewith, is incorporated herein by reference in its entirety.

TECHNICAL FIELD

The present disclosure relates to a galectin-targeting immunotherapy.

BACKGROUND ART

Galectins are members of the lectin family, which show high affinities for β-galactosides. There have been about 15 galectins discovered in mammals, encoded by the LGALS genes, which are numbered in a consecutive manner. Currently only galectin-1, -2, -3, -4, -7, -7B, -8, -9, -9B, 9C, -10, -12, -13, -14, and -16 have been identified in humans.

Galectin-1 (Gal-1) is a member of a highly conserved family of animal lectins binding to N-acetyllactosamine (LacNAc; Galβ1-4GlcNAc)-containing glycoprotein or glycolipids (Non Patent Literature 1: Barondes S H 1994). Gal-1 is significantly upregulated and secreted in many tumors. High levels of Gal-1 are associated with tumor aggressiveness, metastasis, and poor survival for many cancers (Non Patent Literature 2: Astorgues-Xerri L 2014). Previous studies explained that Gal-1 have emerged as novel regulatory checkpoints that promote immune evasive programs by inducing T-cell exhaustion, limiting T-cell survival, favoring expansion of regulatory T cells, de-activating natural killer cells and polarizing myeloid cells toward an immunosuppressive phenotype (Non Patent Literature 3: Banh A 2011). Expression of Galectin-1 is upregulated by hypoxic condition and glycosylation-dependent galectin-receptor interactions control angiogenesis (Non Patent Literature 4: Rabinovich 2014) (Non Patent Literature 5: Xu-Yun Zhao 2010). Thus, targeting galectin-glycan interactions may interfere tumor progression by simultaneously augmenting antitumor immunity and suppressing aberrant angiogenesis (Non Patent Literature 6: Thijssen V L 2006).

Due to the essential and multifunctional role of galectin and/or their binding glycoconjugates in the process of cancer development and prognosis, different candidate inhibitors that could block the interaction between these molecules have been proposed as potential anticancer drugs (Non Patent Literature 7: Lucile Astorgues-Xerri 2014). To date, most known galectin antagonists are glycomimetics and are derivatives or analogs of galactoside, targeting the canonical carbohydrate-binding site of galectins (Non Patent Literature 8: Koonce N A 2017). Peptide and antibody Gal-1 inhibitors are also reported its ability to antagonize galectin-receptor interactions (Non Patent Literature 9: Diego O. Croci 2012, Non Patent Literature 10: van der Schaft D W 2002).

Galectin-3 (Gal-3) is a member of a highly conserved family of animal lectins binding to β-galactoside-containing glycoconjugates (glycoprotein or glycolipids) (Non Patent Literature 11: M. A. Henderson N C 2006, Non Patent Literature 12: Mourad-Zeidan A A 2008). Gal-3 is unique among other Galectin-family proteins in its structure composed of two domains: a carboxyl-terminal domain that contains the carbohydrate-binding region and an amino-terminal domain consisting primarily of tandem repeat of nine amino acids to cross-link carbohydrate and noncarbohydrate ligands (FIG. 12A) (Non Patent Literature 13: Liu 1990, Non Patent Literature 1: Barondes S H 1994). It is secreted by various types of cells including monocytes, macrophages and epithelial cells, but mainly by macrophage (Non Patent Literature 14: Reynolds 2005, Non Patent Literature 15 MacKinnon AC 2008). Secreted extracellular Gal-3 forms homo-dimer or pentamer and it is important for the biological function. The N-terminal domain of galectin-3 has been demonstrated to be important for the formation of protein oligomers (FIG. 12 B) (Non Patent Literature 13: Liu 1990, Non Patent Literature 16: Dumic J 2006, Non Patent Literature 17: Kuklinski S 1998, Non Patent Literature 18: Lepur A 2012) The released protein can function as an extracellular molecule to activate cells, mediate cell-cell and cell-ECM interactions, induce migration of various types of cell, and negatively regulate T cell receptor signaling (Non Patent Literature 19: Yang R Y 1996). Gal-3 was shown to be increased in various models of fibrotic diseases and patients including lung fibrosis, liver fibrosis, systemic sclerosis and cardiac fibrosis (Non Patent Literature 20: M. A. Henderson NC 2008, Non Patent Literature 21: Barman, et al. 2019, Non Patent Literature 22: Nishi Y 2007, Non Patent Literature 23: De Boer 2010). This suggests that Gal-3 may be an important mediator of and effective therapeutic target for tissue fibrosis. To date, preclinical and clinical studies of investigational Galectin-3 inhibitors showed protection against fibrotic disorders (Non Patent Literature 24: Nikhil Hirani 2017, Non Patent Literature 25: Yu L 2013).

One of the major success stories in medicine during the last 100-150 years is vaccines targeting various infectious diseases. Vaccines have, together with antibiotics, likely been more important for human health than any other part of human. Because of the success of vaccines, the interest in using vaccine technology for the treatment of noninfectious diseases such as allergies, autoimmunity, and cancer is increasing. However, the targets for these diseases are in general self-antigens, which may pose problems with efficacy. It is considerably difficult to induce a strong antibody response to a self-antigen compared with a non-self-antigen-bacterial, viral, or parasite protein-because of tolerance mechanisms (Non Patent Literature 26: Hellman 2008, Non Patent Literature 27: Falk Saupe 2015).

Alphaviruses comprise a set of genetically, structurally, and serologically related mosquito-borne viruses of the Togaviridae family. The alphaviruses include Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2.

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's EngerixR (hepatitis B virus) and CervarixR (human papillomavirus), and Merck and Co., Inc.'s Recombivax HBR (hepatitis B virus) and GardasilR (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination.

Up to now, VLP-based vaccines have been produced for more than 30 different viruses that infect human and other animals. The examples include AAV (Adeno-associated virus), H5N3 (Avian influenza), BFDV (Budgerigar fledgling disease virus), BTV (Bluetongue virus), Ebola, Enterovirus 71, GHPV (Goose hemorrhagic polyoma virus), HBV (Hepatitis B virus), HCV (Hepatitis C virus), HDV (Hepatitis δ virus), HEV (Hepatitis E virus), HIV, HPV (Human papillomavirus), IBDV (Infectious bursal disease virus), Influenza A, Influenza A H1N1, Influenza A H3N2, JC polymavirus, Margurg, MS2, IPCV (Indian peanut clump virus), NDV (Newcastle disease virus), No (Norovirus) Nv (Norwalk virus), PhMV (Physalis mottle virus), Polymavirus, PPV (Porcine parvovirus), RHDV (Rabbit hemorrhagic disease virus), Rotavirus, SARS, SIV (Simian immunodeficiency virus), SV40 (Simian virus 40), SVDV (Swine vesicular disease virus) and so on. (Non Patent Literature 28: Expert Rev. Vaccines 9(10), 1149-1176, 2010).

U.S. Pat. No. 9,353,353 (Patent Literature 1) discloses a virus-like particle (VLP) comprising one or more Chikungunya virus viral structural proteins which is useful for formulating a vaccine or antigenic composition for Chikungunya that induces immunity to an infection or at least one symptom thereof. U.S. Pat. No. 9,487,563 (Patent Literature 2) discloses modified alphavirus or flavivirus virus-like particles (VLPs) and methods for enhancing production of modified VLPs for use in the prevention or treatment of alphavirus and flavivirus-mediated diseases. U.S. Pat. No. 9,249,191 (Patent Literature 3) discloses a Chikungunya virus (CHIKV) or Venezuelan equine encephalitis virus (VEEV) virus-like particle, wherein said virus-like particle contains at least one antigen inserted into an E2 envelope protein to form a fusion protein. U.S. Pat. No. 9,969,986 discloses an alphavirus virus-like particle, wherein said virus-like particle comprises an alphavirus viral sturctural protein that comprises an envelope protein E3, wherein said envelope protein E3 is modified to contain at least one foreign antigen inserted into furin cleavage site thereof. The cited references are herein incorporated by reference.

CITATION LIST

The contents of the following references are herein incorporated by reference.

PATENT LITERATURE

[PTL 1]U.S. Pat. No. 9,353,353
[PTL 2]U.S. Pat. No. 9,487,563
[PTL 3]U.S. Pat. No. 9,249,191

Non Patent Literature

[NPL 1] Barondes S H, Cooper D N, Gitt M A, Leffler H. 1994. "Galectins. Structure and function of a large family of animal lectins." J Biol Chem 269:20807-20810.

[NPL 2] Astorgues-Xerri L, Riveiro M E, Tijeras-Raballand A, Serova M, Neuzillet C, Albert S, Raymond E, Faivre S. 2014. "Unraveling galectin-1 as a novel therapeutic target for cancer" Cancer Treat Rev. 40:307-19.

[NPL 3] Banh A, Zhang J, Cao H, Bouley D M, Kwok S, Kong C, et al. 2011. "Tumor galectin-1 mediates tumor growth and metastasis through regulation of T-cell apoptosis" Cancer Res 71:4423-31.

[NPL 4] Rabinovich, Mariana SalatinoEmail authorDiego O. CrociDiego J. LaderachDaniel CompagnoLucas GentiliniTomas Dalotto-MorenoL. Sebastian Dergan-DylonSantiago P. Méndez-HuergoMarta A. ToscanoJuan P. CerlianiGabriel A. 2014. "Regulation of Galectins by Hypoxia and Their Relevance in Angiogenesis: Strategies and Methods" Methods in Molecular Biology Galectins pp 293-304.

[NPL 5] Xu-Yun Zhao, Ting-Ting Chen, Li Xia, Meng Guo, Ying Xu, Fei Yue, Yi Jiang, Guo-Qiang Chen, Ke-Wen Zhao. 2010. "Hypoxia inducible factor-1 mediates expression of galectin-1: the potential role in migration/invasion of colorectal cancer cells." Carcinogenesis 31(8); 1367-1375.

[NPL 6] Thijssen V L, Postel R, Brandwijk R J, Dings R P, Nesmelova I, Satijn S, Verhofstad N, Nakabeppu Y, Baum L G, Bakkers J, Mayo K H, Poirier F, Griffioen A W. 2006. "Galectin-1 is essential in tumor angiogenesis and is a target for antiangiogenesis therapy." Proc Natl Acad Sci USA. 103 (43):15975-80.

[NPL 7] Lucile Astorgues-Xerri, Maria E. Riveiro, Annemilaï Tijeras-Raballand, Maria Serova. 2014. "Unraveling galectin-1 as a novel therapeutic target for cancer." Cancer Treatment Reviews 307-319.

[NPL 8] Koonce N A, Griffin R J, Dings R P M. 2017. "Galectin-1 Inhibitor OTX008 Induces Tumor Vessel Normalization and Tumor Growth Inhibition in Human Head and Neck Squamous Cell Carcinoma Models." Int J Mol Sci. 9(18); 2671.

[NPL 9] Diego O. Croci, Mariana Salatino, Natalia Rubinstein, Juan P. Cerliani, Lucas E. Cavallin, Howard J. Leung, Jing Ouyang, Juan M. Ilarregui, Marta A. Toscano, Carolina I. Domaica, Maria C. Croci, Margaret A. Shipp, Enrique A. Mesri, Adriana Albini, Gabriel. 2012. "Disrupting galectin-1 interactions with N-glycans suppresses hypoxia-driven angiogenesis and tumorigenesis in Kaposi's sarcoma." J. Exp. Med 209:1985-2000.

[NPL 10] van der Schaft D W, Dings R P, de Lussanet Q G, van Eijk L I, Nap A W, Beets-Tan R G, Bouma-Ter Steege J C, Wagstaff J, Mayo K H, Griffioen A W. 2002. "The designer anti-angiogenic peptide anginex targets tumor endothelial cells and inhibits tumor growth in animal models." FASEB J. 16(14):1991-3.

[NPL 11] Henderson N C, Mackinnon A C, Farnworth S L, Poirier F, Russo F P, Iredale J P, Haslett C, Simpson K J, Sethi T. 2006. "Galectin-3 regulates myofibroblast activation and hepatic fibrosis." Proc Natl Acad Sci USA 103(13):5060-5.

[NPL 12] Mourad-Zeidan A A, Melnikova V O, Wang H, Raz A, and Bar-Eli M. 2008. "Expression profiling of Galectin-3-depleted melanoma cells reveals its major role in melanoma cell plasticity and vasculogenic mimicry." Am J Pathol 173:1839-1852.

[NPL 13] Liu, T F. 1990. "Molecular biology of IgE-binding protein, IgE-binding factors, and IgE receptors." Crit Rev Immunol. 10(3):289-306.

[NPL 14] Reynolds, H Y. 2005. "Lung inflammation and fibrosis: an alveolar macrophage-centered perspective from the 1970s to 1980s." Am J Respir Crit Care Med 171:98-102.

[NPL 15] MacKinnon A C, Farnworth S L, Hodkinson P S, Henderson N C, Atkinson K M, Leffler H, Nilsson U J, Haslett C, Forbes S J, and Sethi T. 2008. "Regulation of alternative macrophage activation by galectin-3." J Immunol 180:2650-2658.

[NPL 16] Dumic J, Dabelic S, Flogel M. 2006. "Galectin-3: An open-ended story." BBA-Gen Subjects 1760:616-635.

[NPL 17] Kuklinski S, Probstmeier R. 1998. "Homophilic binding properties of galectin-3: Involvement of the carbohydrate recognition domain." J Neurochem 70:814-823.

[NPL 18] Lepur A, Salomonsson E, Nilsson U J, Leffler H. 2012. "Ligand induced galectin-3 protein self-association." J Biol Chem 287:21751-21756.

[NPL 19] Yang R Y, Hsu D K, and Liu F T. 1996. "Expression of galectin-3 modulates T-cell growth and apoptosis." Proc Natl Acad Sci USA 93:6737-6742.

[NPL 20] Henderson N C, Mackinnon A C, Farnworth S L, Kipari T, Haslett C, Iredale J P, Liu F T, Hughes J, Sethi T. 2008. "Galectin-3 expression and secretion links macrophages to the promotion of renal fibrosis." Am J Pathol. 172 (2):288-98.

[NPL 21] Barman, Scott A, Xueyi Li, Stephen Haigh, Dmitry Kondrikov, Keyvan Mahboubi, Zsuzsanna Bordan, and Stepp W David. 2019. "Galectin-3 is Expressed in Vascular Smooth Muscle Cells and Promotes Pulmonary Hypertension through changes in Proliferation, Apoptosis and Fibrosis." Am J Physiol Lung Cell Mol Physiol. February 6, Epub ahead of print.

[NPL 22] Nishi Y, Sano H, Kawashima T, Okada T, Kuroda T, Kikkawa K, Kawashima S, Tanabe M, Goto T, Matsuzawa Y, Matsumura R, Tomioka H, Liu F T, Shirai K. 2007. "Role of Galectin-3 in Human Pulmonary Fibrosis." Allergol Int. 56(1):57-65.

[NPL 23] De Boer, R. A., Yu, L., and van Veldhuisen, D. J. 2010. "Galectin-3 in cardiac remodeling and heart failure." Curr. Heart Fail. Rep. 7, 1-8.

[NPL 24] Nikhil Hirani, Alison Mackinnon, Lisa Nicol, Jeremy Walker, Paul Ford, Hans Schambye, Anders Pederson, Ulf Nilsson, Hakon Leffler, Tracy Thomas, Danielle Francombe, John Simpson, Michael Gibbons, Toby M. Maher. 2017. "TD139, A Novel Inhaled Galectin-3 Inhibitor for the Treatment of Idiopathic Pulmonary Fibrosis (IPF). Results from the First in (IPF) Patients Study." American Journal of Respiratory and Critical Care Medicine 195:A7560.

[NPL 25] Yu L, Ruifrok W P, Meissner M, Bos E M, van Goor H, Sanjabi B, van der Harst P, Pitt B, Goldstein I J, Koerts J A, et al. 2013. "Genetic and pharmacological inhibition of galectin-3 prevents cardiac remodeling by interfering with myocardial fibrogenesis." Circ Heart Fail 6:107-117.

[NPL 26] Hellman, L. 2008. "Therapeutic vaccines against IgE-mediated allergies." Expert Rev Vaccines 7(2):193-208.

[NPL 27] Falk Saupe, Elisabeth J. M. Huijbers, Tobias Hein, Julia Femel, Jessica Cedervall, Anna-Karin Olsson, and Lars Hellman. 2015. "Vaccines targeting self-antigens: mechanisms and efficacy-determining parameters." FASEB J 29(8):3253-62.

SUMMARY OF INVENTION

The present disclosure relates to a galectin-targeting immunotherapy.

In a first aspect, the present disclosure provides a virus like particle comprising a viral structural protein and at least one galectin antigen.

In a second aspect, the present disclosure provides an isolated nucleic acid molecule comprising a nucleotide sequence encoding the virus like particle provided in the first aspect of the present application.

In a third aspect, the present disclosure provides a vector comprising the nucleic acid molecule of the second aspect, wherein the vector optionally comprises an expression control sequence operably linked to the nucleic acid molecule.

In a forth aspect, the present disclosure provides a pharmaceutical composition or vaccine composition comprising (a) the virus like particle of the first aspect, the nucleic acid molecule of the second aspect, and/or the vector of the third aspect; and (b) a pharmaceutically acceptable carrier.

In a fifth aspect, the present disclosure provides a galectin-targeting immunotherapy which comprises administering an effective amount of the virus like particle of the first aspect, the nucleic acid molecule of the second aspect, and/or the vector of the third aspect to a subject in need thereof. This method may be useful for treating or preventing a cancer, inflammatory disease, and a fibrotic disease. Methods for modulating an immune response in a subject, for immunostimulating a subject, for producing an antibody against galectin in a non-human mammal; for modulating an immune response in a subject; for immunostimulation in a subject; for inhibiting galectin-glycan interactions in a subject; or for inhibiting a galectin activity is also provided.

In a sixth aspect, the present disclosure provides use of the virus like particle of the first aspect, the nucleic acid molecule of the second aspect, and/or the vector of the third aspect, for the manufacture of a pharmaceutical composition or a kit for immunotherapy, for modulating an immune response in a subject, for immunostimulating a subject, for producing an antibody against galectin in a non-human mammal; for modulating an immune response in a subject; for immunostimulation in a subject; for inhibiting galectin-glycan interactions in a subject.

In a sixth aspect, the present disclosure provides a use of the virus like particle of the first aspect, the nucleic acid molecule of the second aspect and/or the vector of the third aspect for the manufacture of a pharmaceutical composition or a vaccine composition of the forth aspect for immunotherapy, treating or preventing a cancer or inflammatory disease; for producing an antibody against galectin in a mammal; for modulating an immune response; for immunostimulation; for inhibiting galectin-glycan interactions; or for inhibiting a Galectin activity.

14, respectively, from left to right. The far right is a control VLP with no antigen peptide.

Figure 2A:
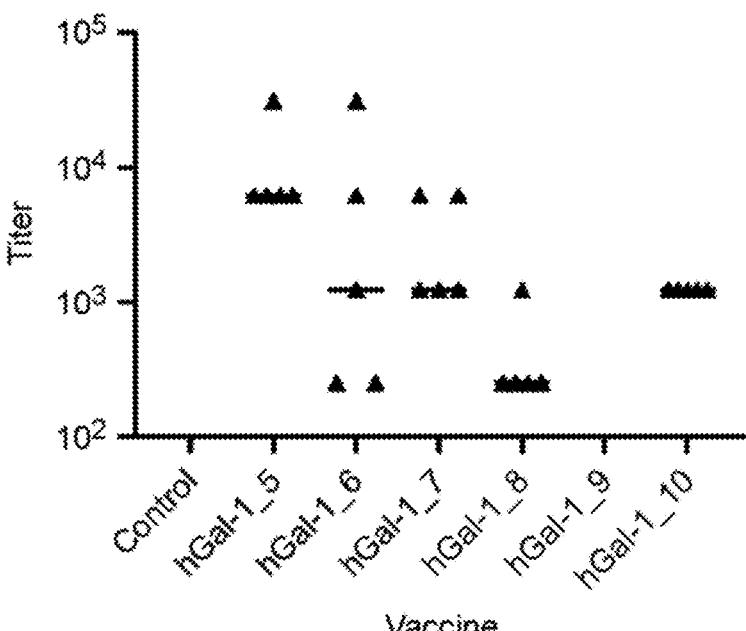

[FIG. 2A] Immunogenicity of CHIKV-VLPs bearing Gal-1 epitope peptides #5-#10 (derived from human) in naïve BALB/c mice

Figure 2B:
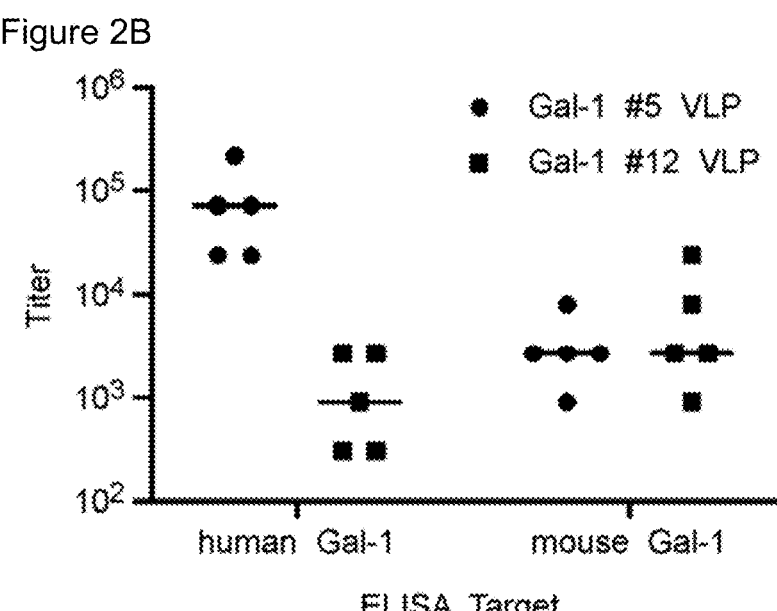

[FIG. 2B] Immunogenicity of CHIKV-VLPs bearing Gal-1 epitope peptides #5 (derived from human) and #12 (derived from mouse) in naïve BALB/c mice.

Figure 3A:
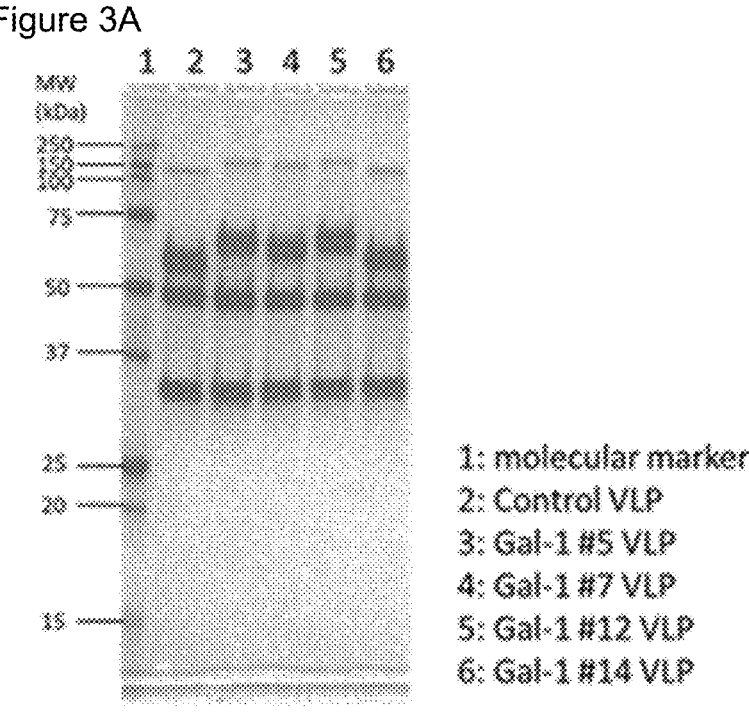

[FIG. 3A] The expression of VEEV-VLPs bearing a Gal-1 epitope peptide.

Figure 3B:
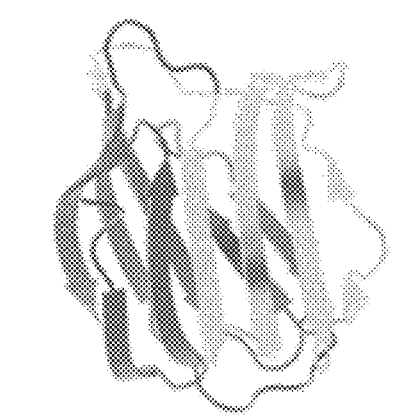

[FIG. 3B] A 3D structure of the Gal-1 protein. Gal-1 epitope peptide #5 and #12 encode four β-sheet S3, S4, S5 and S6 near the carbohydrate recognition domain (CRD).

Figure 3C:
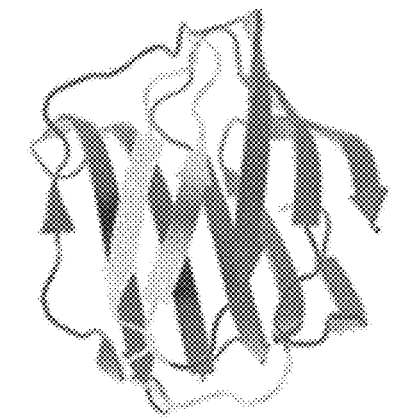

[FIG. 3C] A 3D structure of the Gal-1 protein. The Gal-1 peptide #7 and #14 encodes F4 and F5 β-sheet which might be important in homophilic dimerization.

Figure 3D:
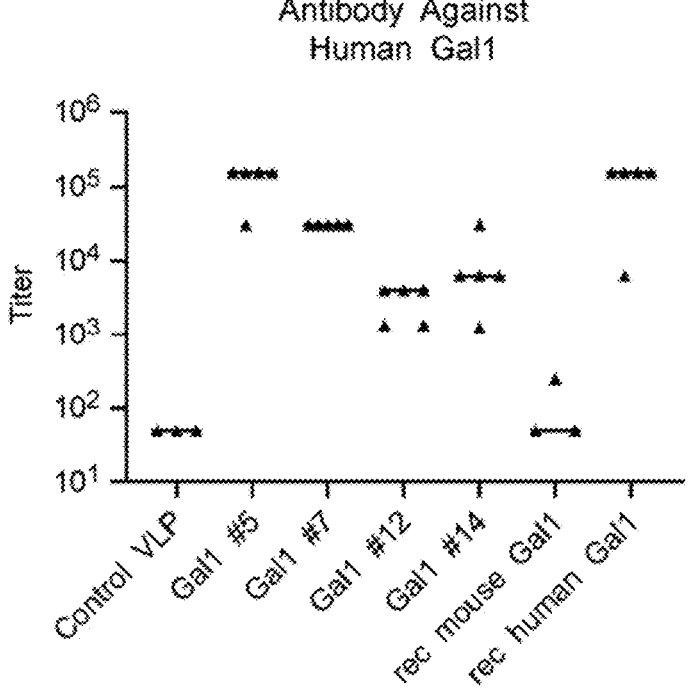

[FIG. 3D] Anti-human Gal-1 antibody titer in mice sera immunized with VEEV-VLPs bearing Gal-1 epitope peptides #5, #7, #12 and #14.

Figure 3E:
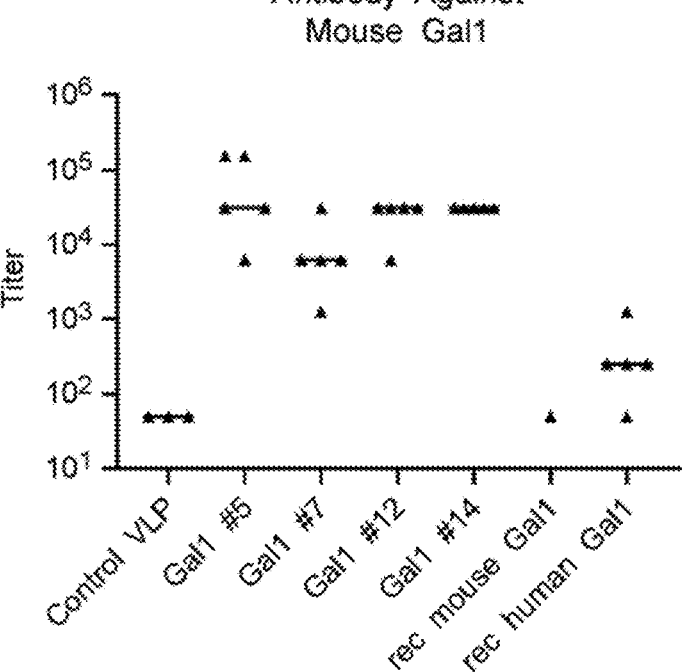

[FIG. 3E] Anti-mouse Gal-1 antibody titer in mice sera immunized with VEEV-VLP bearing Gal-1 epitope peptides #5, #7, #12 and #14.

Figure 3F:
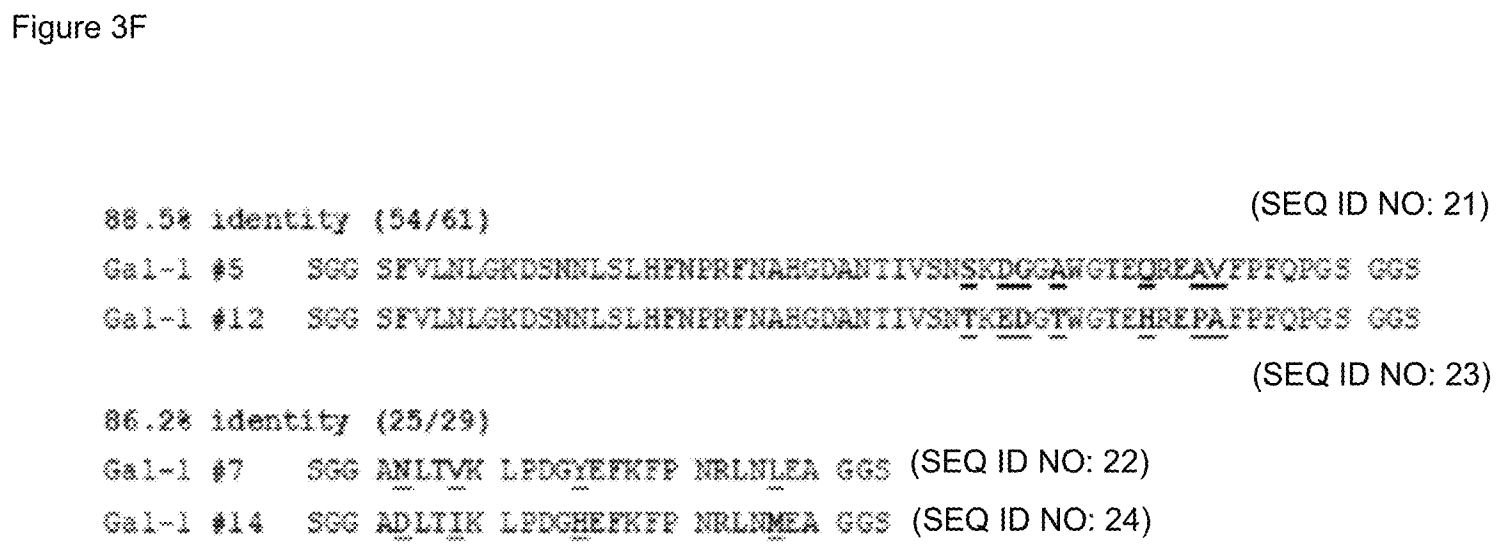

[FIG. 3F] Comparison between Gal-1 epitope peptides derived from human Gal-1 and Mouse Gal-1. Amino acids different between them are underlined.

Figures 4A, 4B:
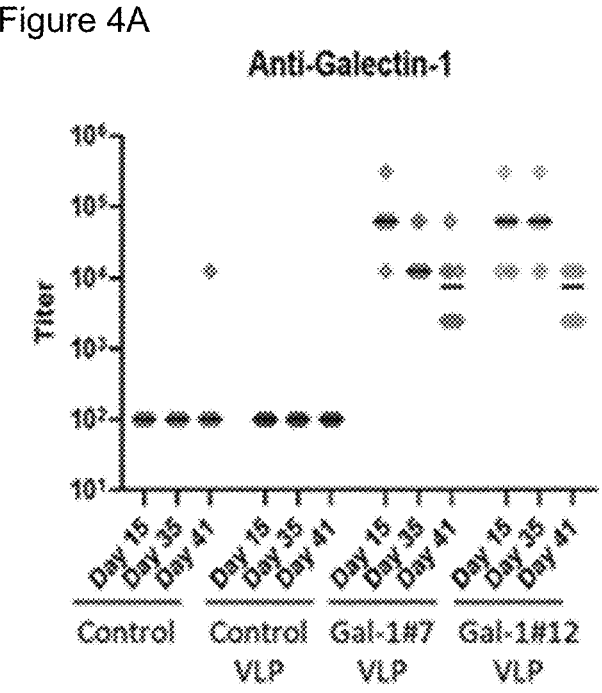

[FIG. 4A] Anti-mouse Gal-1 antibody titer in mice sera immunized with CHIKV-VLPs bearing Gal-1 epitope peptide #7 and #12.

[FIG. 4B] Antibody titer against CHIKV spike protein in mice sera immunized with VEEV-VLPs bearing Gal-1 epitope peptides #7 and #12.

Figure 4C:
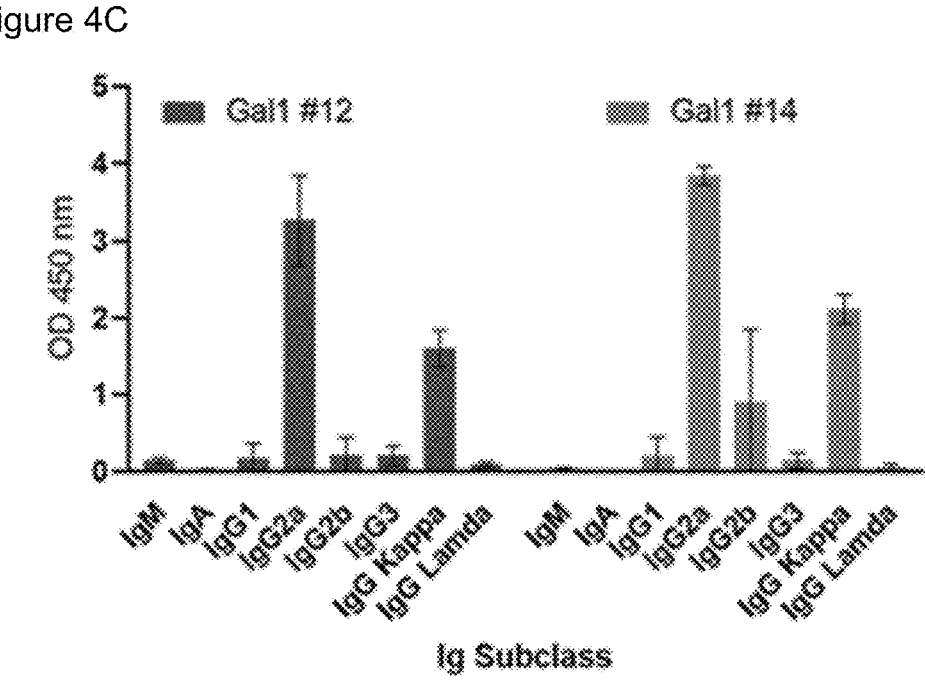

[FIG. 4C] Immunoglobulin subclasses of the antibodies in mice sera immunized with CHIKV-VLP bearing Gal-1 epitope peptides #12 and #14.

Figure 5A:
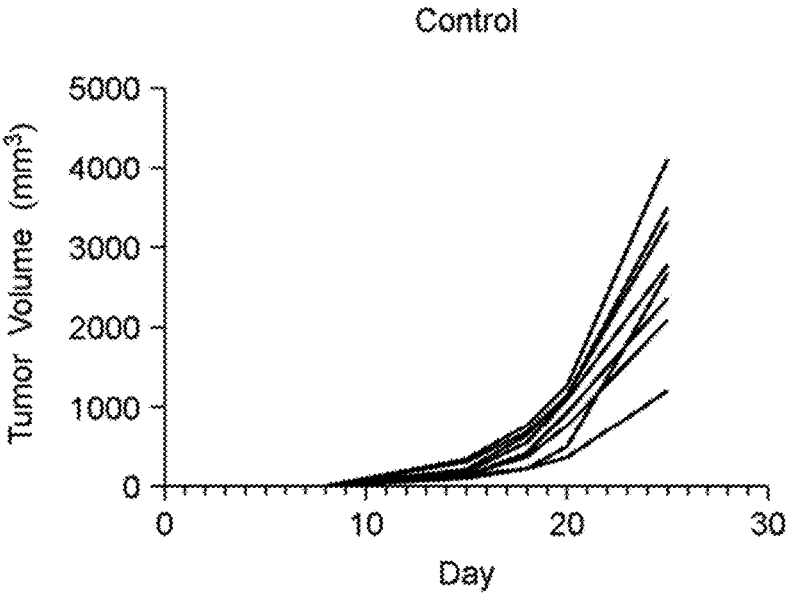

[FIG. 5A] Effects of the CHIKV-VLPs bearing Gal-1 epitope peptides #7 and #12 on Lewis lung carcinoma in mice. (Control)

Figure 5B:
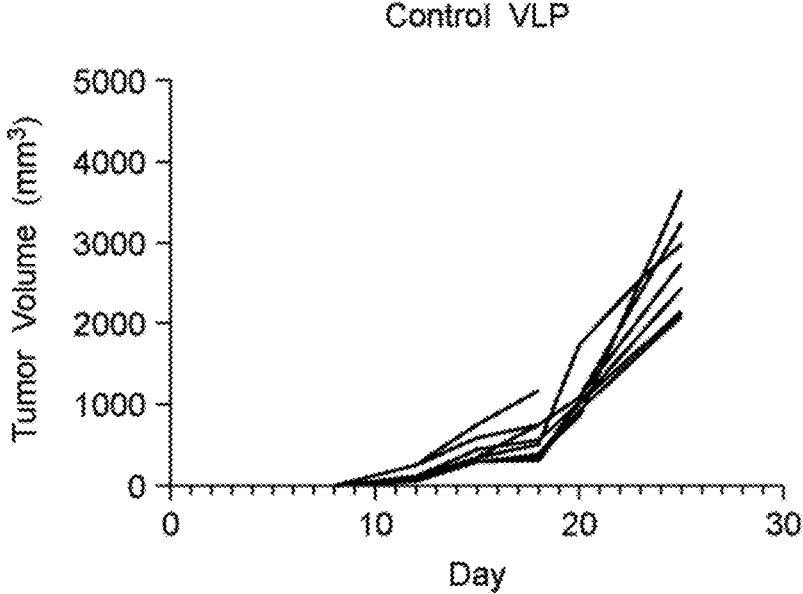

[FIG. 5B] Effects of the CHIKV-VLPs bearing Gal-1 epitope peptides #7 and #12 on Lewis lung carcinoma in mice. (Control VLP)

Figure 5C:
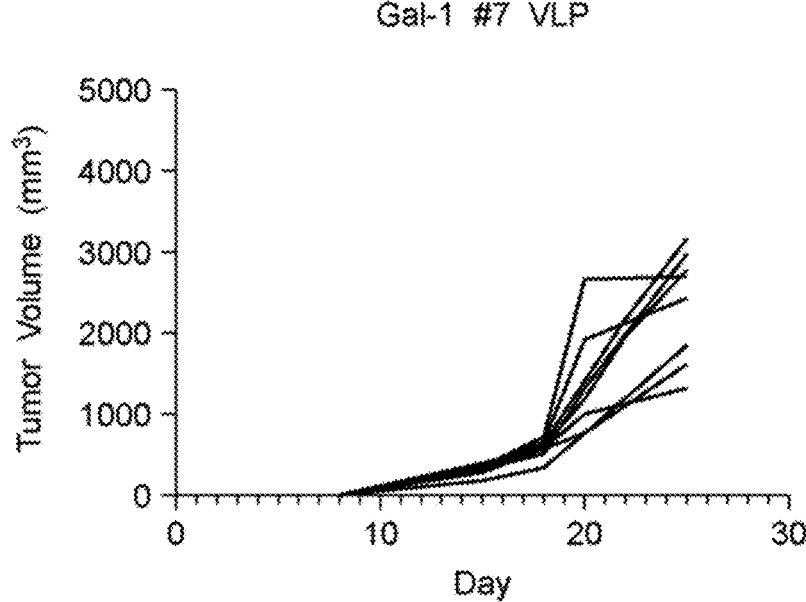

[FIG. 5C] Effects of the CHIKV-VLPs bearing Gal-1 epitope peptides #7 and #12 on Lewis lung carcinoma in mice. (Gal-1 #7 VLP)

Figure 5D:
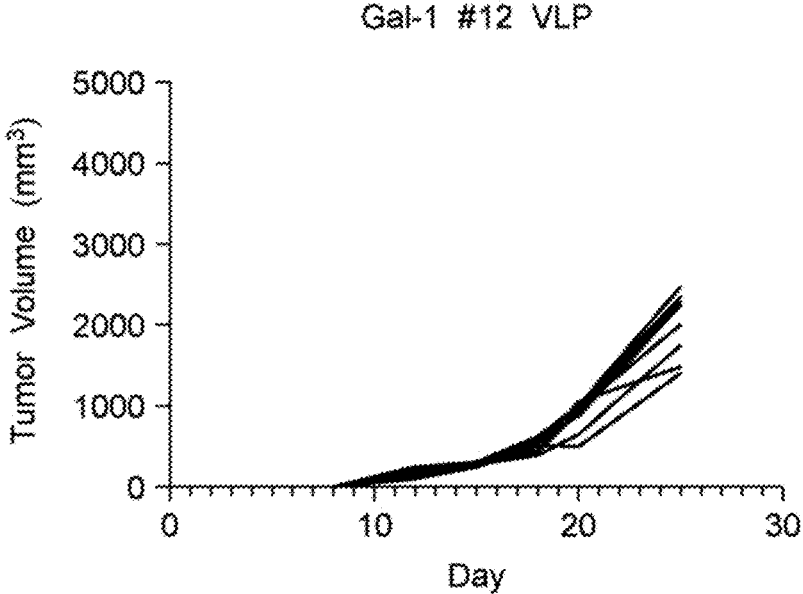

[FIG. 5D] Effects of the CHIKV-VLPs bearing Gal-1 epitope peptides #7 and #12 on Lewis lung carcinoma in mice. (Gal-1 #12 VLP)

Figure 5E:
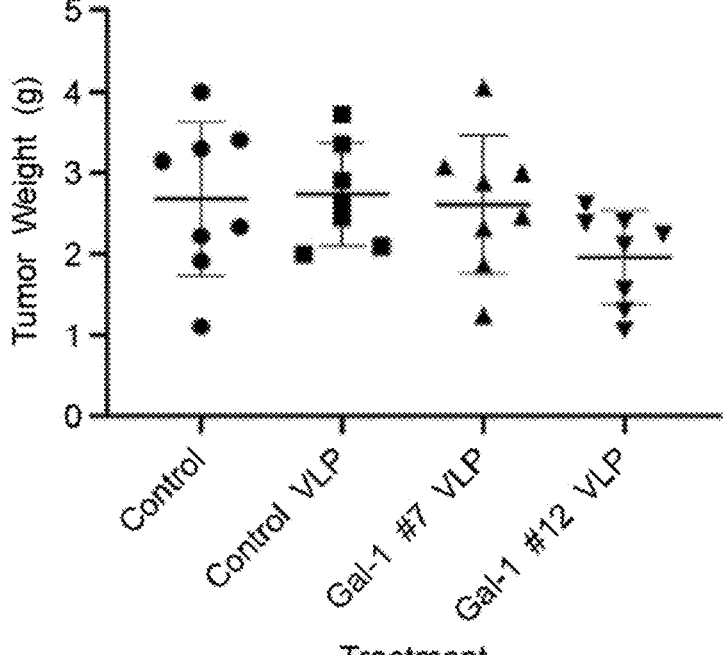

[FIG. 5E] Endpoint tumor weights in each group. Though there was no statistically significant difference in tumor volume (FIG. 5A-D) and (FIG. 5E) between control and VLP treated groups, tumor growth in mice treated with Gal-1 #12 was slower than that of other groups.

Figure 6A:
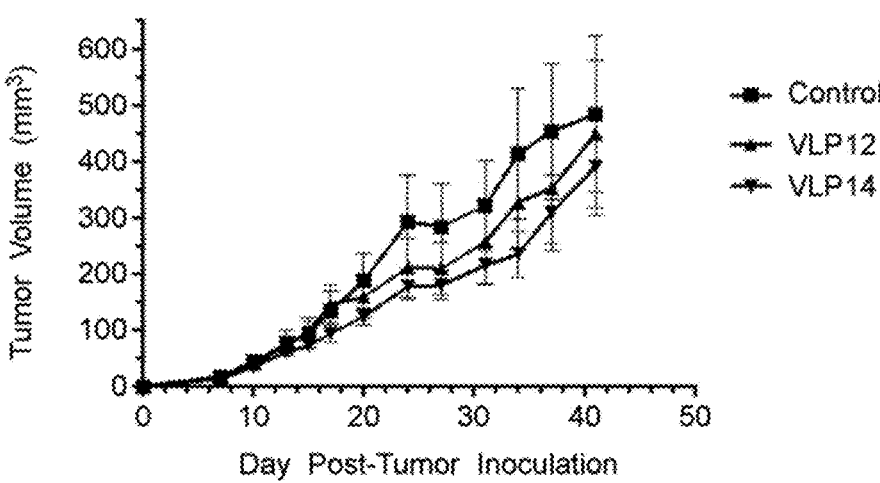

[FIG. 6A] Effects of the CHIKV-VLPs bearing Gal-1 epitope peptides #12 and #14 on mouse HPV+ Head and Neck Squamous Carcinoma Cell model. The tumor growth in mice treated with Gal-1 #14 VLP vaccine was slower than that of control but not statistically significant difference between any groups.

Figure 6B:
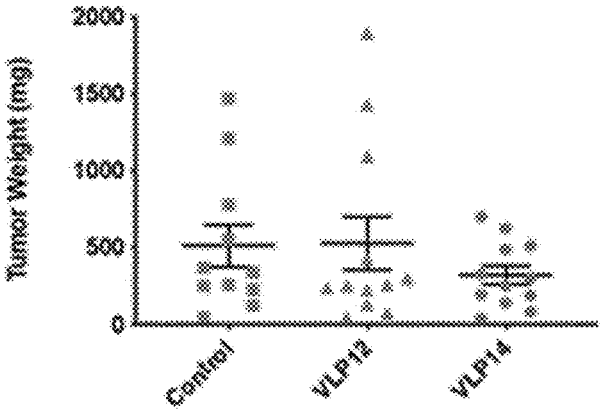

[FIG. 6B] Effects of the CHIKV-VLPs bearing Gal-1 epitope peptides #12 and #14 on the endpoint weight of mouse HPV+ Head and Neck Squamou Carcinoma Cell model.

Figure 7:
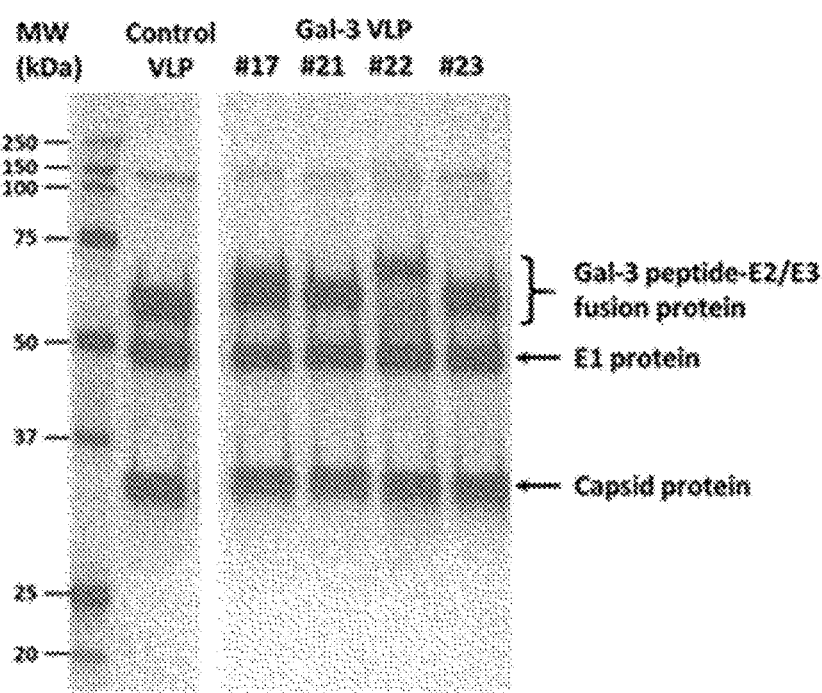

[FIG. 7] Molecular size and purity of VEEV-VLPs bearing Gal-3 epitope peptides #17, #21, #22 and #23 and control VLP.

Figure 8:
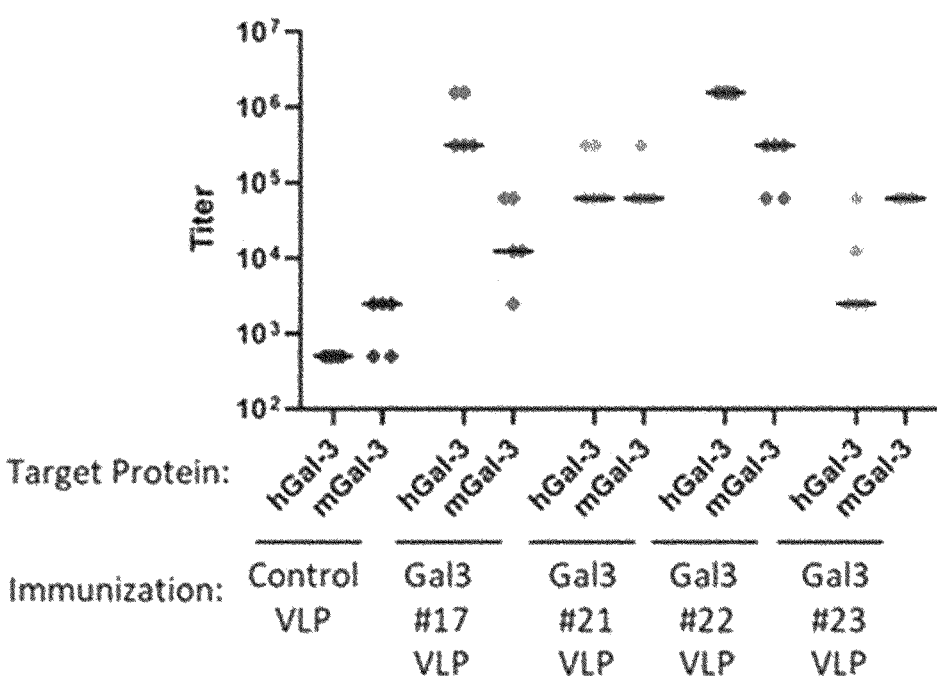

[FIG. 8] Immunogenicity of VEEV-VLPs bearing Gal-3 epitope peptides #17, #21, #22 and #23 in mice.

Figure 9:
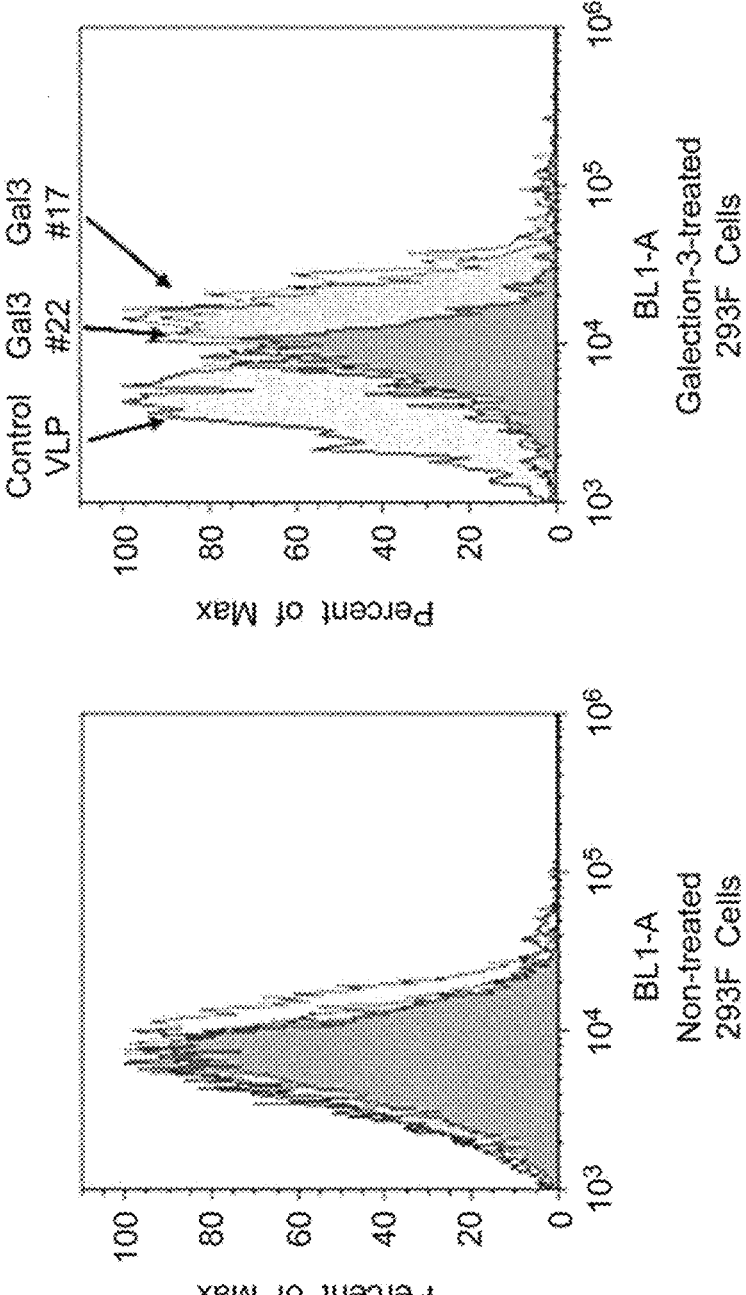

[FIG. 9] Flow cytometry analysis. Sera from mouse immunized with VLPs bearing Gal-3 epitope peptide #17 and #22 were analyzed for the binding to cell surface Gal-3.

Figure 10:
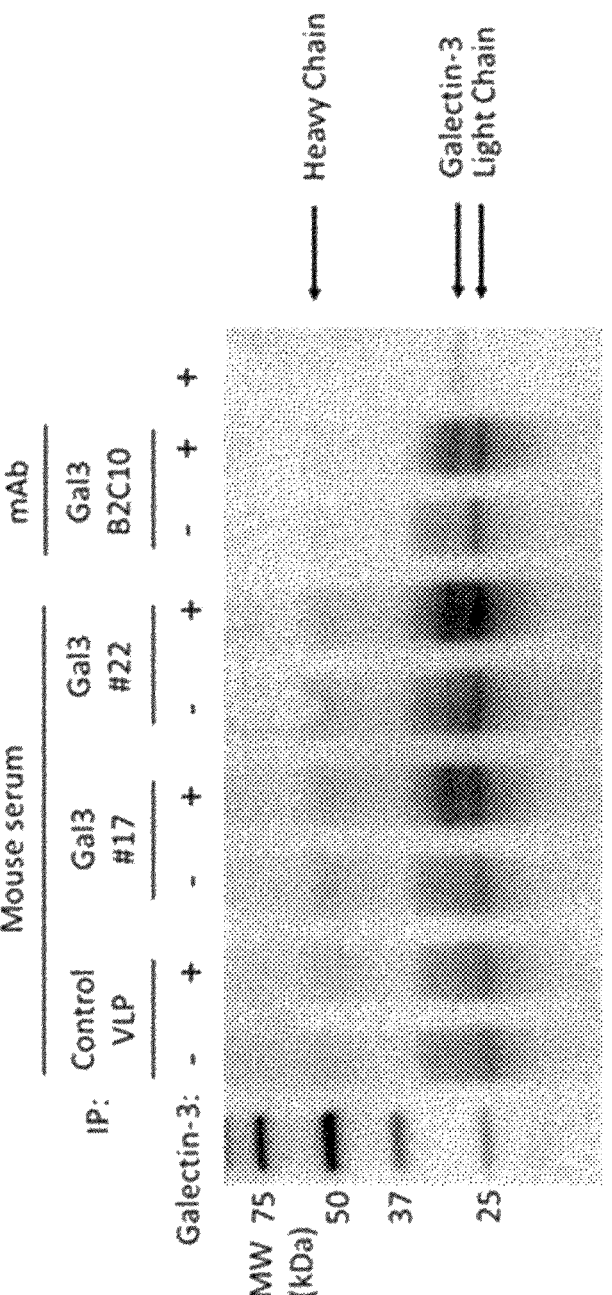

[FIG. 10] Neutralization capacity of anti-Gal-3 antibodies induced in mice by VLP bearing Gal-3 epitope peptide #17 and #22.

Figure 11A:
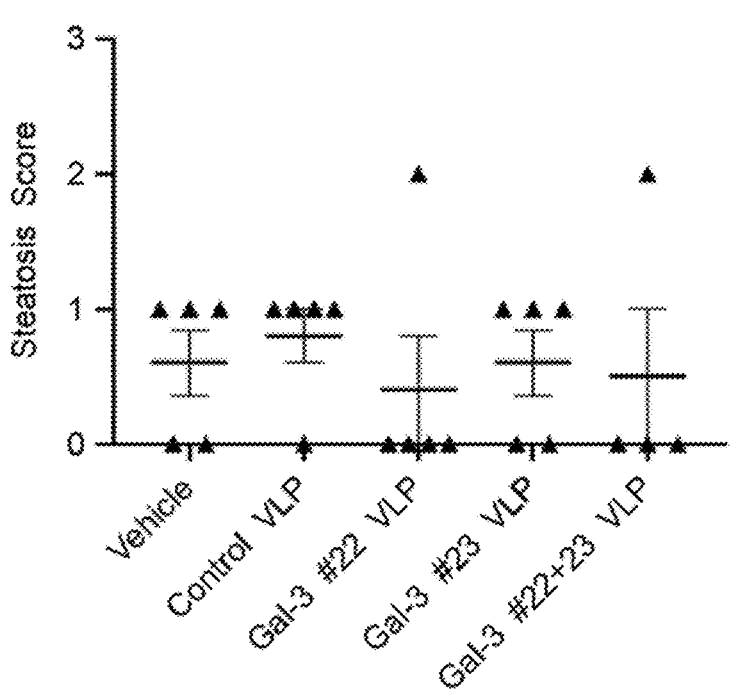

[FIG. 11A] Effects of VLPs bearing Gal-3 epitope peptide #22 and #23 on the mouse STAM non-alcoholic steato hepatitis (NASH) model. (Steatosis Score)

Figure 11B:
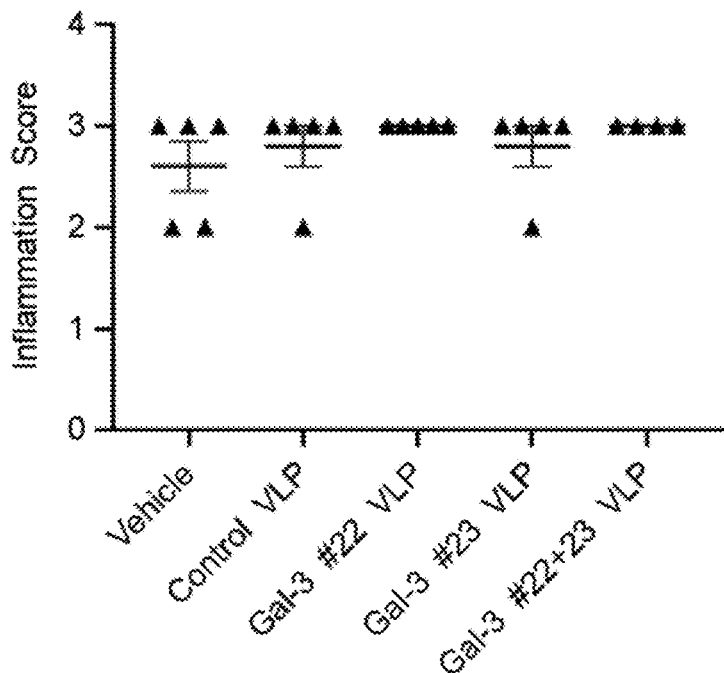

[FIG. 11B] Effects of VLPs bearing Gal-3 epitope peptide #22 and #23 on a mouse STAM non-alcoholic steato hepatitis (NASH) model. (Inflammation Score)

Figure 11C:
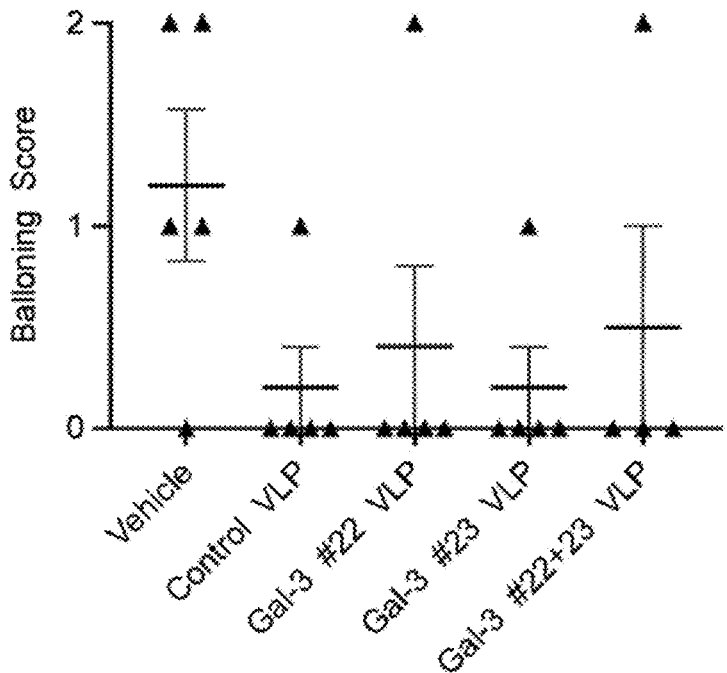

[FIG. 11C] Effects of VLPs bearing Gal-3 epitope peptide #22 and #23 on a mouse STAM non-alcoholic steato hepatitis (NASH) model. (Ballooning Score)

Figure 12A:
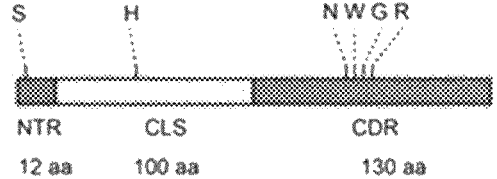
Figure 12B:
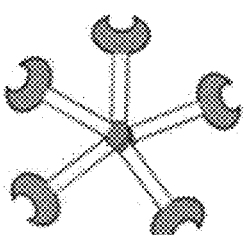

[FIG. 12] (A) Galectin-3 protein structure consists of N terminal Domain, which has a N terminal Region of 12 amino acids containing serin 6 (6) phosphorylation site and a 100 aa long collagen like repeat sequence. The carbohydrrecoginition domain (CDR) 130 aa comprise the C-terminal and contains the NWGR motif; (B) Pentameric structure of Galectin-3.

DETAILED DESCRIPTION

Definitions

By "agent" is meant any small molecule chemical compound, antibody, nucleic acid molecule, or polypeptide, or fragments thereof.

As used herein, the term "adjuvant" is meant a compound that, when used in combination with a specific immunogen in a formulation, will augment, alter or modify the resultant immune response. In certain embodiments, the adjuvant is used in combination with a VLP. In other embodiments, the adjuvant is used in combination with a DNA vaccine. Modification of the immune response includes intensification or broadening the specificity of either or both antibody and cellular immune responses. Modification of the immune response can also mean decreasing or suppressing certain antigen-specific immune responses.

As used herein, "ameliorate" is meant decrease, suppress, attenuate, diminish, arrest, or stabilize the development or progression of a disease or a symptom thereof.

As used herein, "alteration" is meant a change in an amino acid or nucleotide at a specified position with reference to a polypeptide sequence or polynucleotide sequence. As used herein, an alteration includes a substitution, deletion, or insertion of an amino acid or nucleotide at a specified position of a polypeptide or polynucleotide. In some embodiments, an alteration in an alphavirus capsid protein nuclear localization signal includes substitution of a charged amino acid (e.g., lysine or arginine) with an uncharged amino acid (e.g., alanine or asparagine, or any amino acid except a basic charged amino acid such as lysine or arginine).

As used herein, "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein, "comprises," "comprising," "containing" and "having" and the like can have the meaning ascribed to them in U.S. Patent law and can mean "includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "detect" is meant identifying the presence, absence or amount of the analyte to be detected.

As used herein, "disease" is meant any condition or disorder that damages or interferes with the normal function of a cell, tissue, or organ.

As used herein, "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, "isolated polynucleotide" is meant a nucleic acid molecule (e.g., a DNA) that is free of the genes which, in the naturally-occurring genome of the organism from which the nucleic acid molecule of this disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

As used herein, "isolated polypeptide" is meant a polypeptide of this disclosure that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of this disclosure. An isolated polypeptide of this disclosure may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

As used herein, "reduces" is meant a negative alteration of at least 10%, 25%, 50%, 75%, or 100%.

As used herein, "reference" is meant a standard or control condition.

As used herein, "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

As used herein, "specifically binds" is meant a compound or antibody that recognizes and binds a polypeptide or protein, but which does not substantially recognize and bind other molecules in a sample, for example, a biological sample, which naturally includes the polypeptide or protein.

As used herein, "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

DETAILED DESCRIPTION OF THE INVENTION

In this disclosure, a virus like particle comprising a viral structural protein and a galectin antigen is provided.

As used herein, the term "galectin antigen" refers to any antigenic structure derived from any of galectin proteins which can be recognized by the immune system and/or that stimulates a cell-mediated immune response and/or stimulates the generation of antibodies specific to the antigen. The galectin epitope peptide may be a fragment of a naturally occurring galectin protein, or a fragment of a naturally occurring galectin protein with some modifications. The naturally occurring galectin protein may be galectin-1 (Gal-1) or galectin-3 (Gal-3). Galectin protein may preferably human galectin protein and especially, human galectin-1 or human galectin-3 protein. In one embodiment, the modified fragment has at least 80%, 85%, 90%, 95% or 98% amino acid sequence identity to a fragment of the naturally occurring galectin protein. In one embodiment, the modified peptide fragment is a mutant where at most 10% of the amino acids are deleted, substituted, and/or added based on a fragment of the naturally occurring galectin protein.

Amino acid sequences of naturally occurring human galectin-1 and human galectin-3 are as follows:

Galectin-1 [*Homo sapiens*]

(SEQ ID NO: 7)

MACGLVASNLNLKPGECLRVRGEVAPDAKSFVLNLGKDSNNLCLHFNPRF

NAHGDANTIVCNSKDGGAWGTEQREAVFPFQPGSVAEVCITFDQANLTVK

LPDGYEFKFPNRLNLEAINYMAADGDFKIKCVAFD

Galectin-3 [*Homo sapiens*](GenBank Accession No: AAB86584.1)

(SEQ ID NO: 8)

MADNFSLHDALSGSGNPNPQGWPGAWGNQPAGAGGYPGASYPGAYPGQAP

PGAYPGQAPPGAYPGAPGAYPGAPAPGVYPGPPSGPGAYPSSGQPSATGA

YPATGPYGAPAGPLIVPYNLPLPGGVVPRMLITILGTVKPNANRIALDFQ

RGNDVAFHFNPRFNENNRRVIVCNTKLDNNWGREERQSVFPFESGKPFKI

QVLVEPDHFKVAVNDAHLLQYNHRVKKLNEISKLGISGDIDLTSASYTMI

Examples of galectin antigens, i.e. galectin epitope peptides may include the followings:

Gal-1 epitope peptides
5:

(SEQ ID NO: 9)

SFVLNLGKDSNNL<u>S</u>LHFNPRFNAHGDANTIV<u>S</u>NSKDGGAWGTEQREAVFP

FQPGS

7:

(SEQ ID NO: 10)

ANLTVKLPDGYEFKFPNRLNLEA

12:

(SEQ ID NO: 11)

SFVLNLGKDSNNL<u>S</u>LHFNPRFNAHGDANTIV<u>S</u>NTKEDGTWGTEHREPAFP

FQPGS

14:

(SEQ ID NO: 12)

ADLTIKLPDGHEFKFPNRLNMEA

Gal-3 epitope peptides
17:

(SEQ ID NO: 13)

ADNFSLHDALSGSGNPNPQGWPGAWGNQPA

21:

(SEQ ID NO: 14)

YPGASYPGAYPGQAPPGAYPGQAPPGAYPGAPGA

-continued

22:

(SEQ ID NO: 15)

YPGASYPGAYPGQAPPGAYPGQAPPGAYPGAPGAYPGAPAPGVYPGPPSG

PGAYPSSGQPSATGAYPATGPYGA

23:

(SEQ ID NO: 16)

ADSFSLNDALAGSGNPNPQGYPGAWGNQPA

Gal-1 epitope peptide #5 is a fragment derived from human Gal-1 and #12 is the corresponding fragment derived from mouse Gal-1, wherein cysteines in the wild type sequences are replaced with serin (underlined). Gal-1 epitope peptide #7 is a fragment of wild type human Gal-1, and #14 is the corresponding fragment of mouse wild type Gal-1.

Gal-3 epitope peptide #17 is consisting of human N-term Gal-3 epitope peptide. Gal-3 epitope peptides #21 and 22 consisting of human Gal-3 N-term repeat sequence epitope peptide and #22 has longer repeat sequence than that of #21. #23 encodes mouse Gal-3 N-term peptide In this disclosure, "alphavirus" is meant to refer to RNA-containing viruses that belong to the Togaviridae family of viruses. Exemplary Togaviridae viruses include but are not limited to Eastern Equine Encephalitis Virus (EEEV), Venezuelan Equine Encephalitis Virus (VEEV), Everglades Virus, Mucambo Virus, Pixuna Virus, Western Equine Encephalitis Virus (WEEV), Sindbis Virus, Semliki Forest Virus, Middleburg Virus, Chikungunya Virus (CHIKV), O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, Buggy Creek Virus, Ockelbo virus.

In the virus like particle as provided by the present application, a viral structural protein and an antigen may be linked through at least one first attachment site which is present in the viral structural protein and at least one second attachment site which is present in the antigen.

As used herein, each of "a first attachment site" and "a second attachment site" refers to a site where more than one substance is linked each other.

A viral structural protein and an antigen may be directly or indirectly fused. In one embodiment, one or two linkers may intervene between N-terminal residue of an antigen and a viral structural protein and/or between C-terminal residue of an antigen and a viral structural protein.

An antigen or a viral structural protein can be truncated and replaced by short linkers. In some embodiments, an antigen or a viral structural protein include one or more peptide linkers. Typically, a linker consists of from 2 to 25 amino acids (e.g. 2, 3, 4, 5 or 6 amino acids). Usually, it is from 2 to 15 amino acids in length, although in certain circumstances, it can be only one, such as a single glycine residue.

In one embodiment, a nucleic acid molecule, in which polynucleotide encoding the viral structural protein is genetically fused with polynucleotide encoding the antigen, is expressed in a host cell (e.g. mammalian cells (e.g. 293F cells)) so that the first attachment site and the second attachment site are linked through a peptide bond. In this case, the viral structural protein and the antigen are linked through a peptide bond. Relating to this embodiment, the first attachment site and/or the second attachment site may be genetically modified from the original protein or antigen. For example, the first attachment site is modified from the viral structural protein so that through a linker peptide including SG, GS, SGG, GGS and SGSG, the protein is conjugated with the antigen. When the viral structural protein are chemically conjugated with the antigen, the first attachment site and the second attachment site may be linked through a chemical cross-linker which is a chemical compound. Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

Preferred examples of alphavirus include Chikungunya virus and Venezuelan equine encephalitis virus. Examples of Chikungunya virus may include Chikungunya virus 37997 strain and OPY-1 strain. Examples of Venezuelan equine encephalitis virus may include Venezuelan equine encephalitis virus TC-83 strain.

Viral structural protein may include a capsid protein, and/or an envelope protein, a fragment thereof or a complex thereof. Thus, viral structural protein used for the present application may comprise a capsid protein and/or an envelope protein and/or a fragment or derivative thereof. In one embodiment, the virus like particle provided by this disclosure comprises capsid, E3, E2 and E1 proteins, and a galectin antigen.

Preferably, an antigen may be linked to the Chikungunya virus viral structural protein or Venezuelan equine encephalitis virus viral structural protein as a fusion protein produced by way of genetic engineering.

Under physiological conditions, E3 can be dissociated from E2 after furin cleavage. In one embodiment, the furin cleavage site located in E3 may be mutated to prevent furin site from cleaving. For example, an antigen can be inserted into the furin cleavage site to introduce a mutation in the furin cleavage site. In this embodiment, the virus like particle provided may consist of or comprises capsid, E3, E2 and E1 proteins, where E3 is bound to E2 to form a single protein and an antigen is inserted into E3 region. For example, the virus like particle provided by the present application may be formed by assembling 240 capsids, 240 E1 proteins, 240 proteins in each of which E2 is bound to E3 and an antigen is inserted into each of E3 region.

Chikungunya virus viral structural protein or Venezuelan equine encephalitis virus viral structural protein used in the present application may be a naturally occurring viral structural protein or modified protein thereof. The modified protein may be a fragment of the naturally occurring viral structural protein. In one embodiment, the modified protein has at least 70%, 75%, 80%, 85%, 90%, 95% or 98% amino acid sequence identity to a naturally occurring viral capsid and/or envelope protein. In one embodiment, the modified protein is a mutant where at most 10% of the amino acids are deleted, substituted, and/or added based on a naturally occurring viral capsid and/or envelope protein. For example, K64A or K64N mutation may be introduced into a capsid of Venezuelan equine encephalitis virus viral structural protein used in the present application.

An exemplary Chikungunya virus viral structural protein sequence is provided at Genbank Accession No. ABX40006.1 (SEQ ID NO: 1). Another exemplary Chikungunya virus viral structural protein sequence is provided at Genbank Accession No. ABX40011.1 (SEQ ID NO: 2).

An exemplary Venezuelan equine encephalitis virus viral structural protein is shown in SEQ ID NO: 3.

In one embodiment, the first attachment site may comprise an amino group, and preferably an amino group of a lysine residue. The second attachment site may comprise sulfhydryl group, and preferably, a sulfhydryl group of a cysteine.

In one embodiment, a Chikungunya virus like particle or Venezuelan equine encephalitis virus like particle comprising a Chikungunya or Venezuelan equine encephalitis virus viral structural protein and at least one galectin antigen, wherein the at least one galectin antigen is inserted in E3 of the viral structural protein, and the Chikungunya virus viral structural protein or Venezuelan equine encephalitis virus viral structural protein and the galectin antigen are expressed as a fusion protein can be provided. The galectin antigen may be inserted directly or indirectly in E3 of the viral structural protein.

Regarding Chikungunya virus viral structural protein, at least one galectin antigen may be inserted instead of furin cleavage site (RKRR) in E3, from 322R to 325R of SEQ ID NO: 1 or 2, or a site corresponding to furin site (RKRR) from 322R to 325R of SEQ ID NO: 1 or 2. For example, regarding Chikungunya virus viral structural protein, at least one galectin antigen is inserted between residues H at 321-position and S at 326-position of SEQ ID NO: 1 or 2; between P at 320-position and S at 326-position of SEQ ID NO: 1 or 2; or between S at 319-position and S at 326-position of SEQ ID NO: 1 or 2, or the corresponding site. VLP CHI 0.56 vector may be used for preparing Chikungunya virus like particle where the galectin antigen is inserted between residues 321 and 326 of SEQ ID Nos. 1 or 2. When an galectin antigen is inserted between residues 321 and 326 of SEQ ID Nos. 1 or 2, the virus like particle provided by the present application may be Chikungunya virus like particle comprising a complex of E2 and E3, capsid and E1, and wherein the at least one galectin antigen is inserted in E3 region.

Venezuelan equine encephalitis virus viral structural protein, at least one galectin antigen may be inserted instead of furin cleavage site (RKRR) in E3 from 331R to 334R of SEQ ID NO: 3, or a site corresponding to the furin cleavage site from 331R to 334R of SEQ ID NO: 3. For example, regarding Venezuelan equine encephalitis virus viral structural protein, at least one galectin antigen is inserted between G at 330-position and S at 335-position of SEQ ID NO: 3; between P at 329-position and S at 335-position of SEQ ID NO: 3; or between C at 328-position and S at 335-position of SEQ ID NO: 3, or a corresponding site. VLP_VEEV 0.66 vector may be used for preparing Venezuelan equine encephalitis virus like particle where the antigen is inserted between residues 330 and 335 of SEQ ID NO: 3. When an antigen is inserted between residues 330 and 335 of SEQ ID NO: 3, the virus like particle provided by the present application may be Venezuelan equine encephalitis virus like particle comprising a complex of E2 and E3, capsid and E1, and wherein the at least one galectin antigen is inserted into E3 region.

As used herein with respect to amino acid positions of two proteins or amino acid sequences, the term "corresponding to" is used to indicate that the amino acid residue at a specified amino acid position in the first sequence corresponds to or aligns with the amino acid position in the second protein when the two proteins are subjected to standard sequence alignments (e.g., using the BLASTp program). Thus, the amino acid position "A" in the first protein will correspond to the amino acid position "B" in the second sequence if residues at positions "A" and "B" correspond to each other in a sequence alignment.

The viral structural protein of Chikungunya virus as well as Venezuelan equine encephalitis comprise capsid, E1, E2, 6K and E3. 6K is naturally cleaved during the process of assemble and removed from the VLPs. In the present specification and claims, "viral structural protein" refers not only those having 6K, but also after 6K is removed.

6K sequences of the CHIKV and VEEV used in the working examples are as follows: CHIKV OPY-1 Strain, 6K: 749-809aa of SEQ ID NO: 1 atyqeaaiylwneqqplfwlqa-liplaalivlcnclrllpcccktlaflavmsvgahty sa (SEQ ID NO: 4) CHIKV 37997 strain, 6K: 749-809aa of SEQ ID NO: 2 atyyeaaaylwneqqplfwlqaliplaalivlcnclkllpcccktlaflavmsi-gahty sa (SEQ ID NO: 5) VEEV TC-83strain, 6K: 758-813aa of SEQ ID NO: 3 ettwesldhlwnnnqqmfwiqlliplaaliv-vtrllrcvccvvpflvmagaagaga (SEQ ID NO: 6)

Nucleic acid molecules provided herein include any nucleic acid molecule that encodes a polypeptide of this disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of this disclosure include any nucleic acid molecule that encodes a polypeptide of this disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% forma-mide. Stringent temperature conditions will ordinarily include temperatures of at least about 30° C., more prefer-ably of at least about 37° C., and most preferably of at least about 42° C. Varying additional parameters, such as hybrid-ization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodi-ment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybrid-ization will also vary in stringency. Wash stringency condi-tions can be defined by salt concentration and by tempera-ture. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS.

Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Tech-niques, 1987, Academic Press, New York); and Sambrook et al., Molecular Cloning: A Laboratory Manual, Cold Spring Harbor Laboratory Press, New York. By "substantially iden-tical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Pref-erably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, iso-leucine, leucine; aspartic acid, glutamic acid, asparagine, glutamine; serine, threonine; lysine, arginine; and phenyl-alanine, tyrosine. In an exemplary approach to determining the degree of identity, a BLAST program may be used, with a probability score between e<"3> and e<"100> indicating a closely related sequence.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

In some embodiments of this disclosure, proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host, see U.S. patent publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g., baculovirus) for expression in any cell. A person with skill in the art understands that various subcloning methods are available and are possible.

An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, as the term is used herein, because it is readily manipulatable by standard techniques known to those of ordinary skill in the art.

Polypeptide Expression

In general, VLPs comprising an alfavirus viral structural protein and at least one gelactin antigen may be produced by transforming a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to this disclosure. A polypeptide of this disclosure may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., supra). Non limiting examples of insect cells are, *Spodoptera frugiperda* (Sf) cells, e.g., Sf9, Sf21, *Trichoplusia ni* cells, e.g., High Five cells, and *Drosophila* S2 cells. Examples of fungi (including yeast) host cells are *S. cerevisiae, Kluyveromyces lactis* (*K lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Methods of cloning said proteins are known in the art. For example, the gene encoding a specific alphavirus viral structural protein, e.g., a CHIKV or VEEV viral structural protein can be isolated by RT-PCR from polyadenylated mRNA extracted from cells which had been infected with said virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

This disclosure further provides nucleotides that encode proteins, including chimeric molecules, cloned into an expression vector that can be expressed in a cell that provides for the formation of VLPs. An "expression vector" is a vector, such as a plasmid, that is capable of promoting expression, as well as replication of a nucleic acid incorporated therein.

Typically, the nucleic acid molecule to be expressed is "operably linked" to a promoter and/or enhancer, and is subject to transcription regulatory control by the promoter and/or enhancer.

A variety of expression systems exist for the production of the polypeptides of this disclosure. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Constructs and/or vectors provided herein comprise alphavirus polynucleotides that encode structural protein, including envelope proteins or capsid proteins or portions thereof as described herein. The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with this disclosure comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBacl pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, infect, or transform and can express viral proteins, including those described herein, into eukaryotic cells and/or prokaryotic cells. Thus, this disclosure provides for host cells which comprise a vector (or vectors) that contain nucleic acids which code for alphavirus viral structural genes, including capsid, E3, E2, 6K, and E1 or portions thereof, and/or any chimeric molecule described above, and permit the expression of alphavirus viral structural genes, including capsid E3, E2, 6K, and E1, or portions thereof, and/or any chimeric molecule described above in said host cell under conditions which allow the formation of VLPs.

In one embodiment, said vector is a recombinant baculovirus. In another embodiment, said recombinant baculovirus is transfected into an insect cell. In a preferred embodiment, said cell is an insect cell. In another embodiment, said insect cell is a Sf9 cell.

In another embodiment, said vector and/or host cell comprises nucleotides that encode alphavirus genes, including capsid, E3, E2, 6K, and E1, or portions thereof as described.

In another embodiment, said vector and/or host cell consists essentially of alphavirus capsid, E3, E2, 6K, and E1, or portions thereof as described herein. In a further embodiment, said vector and/or host cell consists of alphavirus protein comprising capsid, E3, E2, 6K, and E1, or portions thereof, as described herein. These vector and/or host cell contain alphavirus core, E3, E2, 6K, and E1, or portions thereof, as described herein, and may contain additional cellular constituents such as cellulVLProteins, baculovirus proteins, lipids, carbohydrates etc.

One particular bacterial expression system for polypeptide production is the *E. coli* pET expression system (Novagen, Inc., Madison, Wis). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, a recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Pharmaceutical Compositions and Administration

This disclosure features pharmaceutical compositions that comprise VLPs as described herein. The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of this disclosure. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In certain embodiments, the VLP composition is supplied in liquid form, for example in a sealed container indicating the quantity and concentration of the VLP composition.

Preferably, the liquid form of the VLP composition is supplied in a hermetically sealed container at least about 50 μg/ml, more preferably at least about 100 μg/ml, at least about 200 μg/ml, at least 500 μg/ml, or at least 1 mg/ml.

Alternatively, the vaccine formulation is administered intranasally, either by drops, large particle aerosol (greater than about 10 microns), or spray into the upper respiratory tract or small particle aerosol (less than 10 microns) or spray into the lower respiratory tract. While any of the above routes of delivery results in an immune response, intranasal administration confers the added benefit of eliciting mucosal immunity at the site of entry of many viruses, including alphaviruses, for example CHIKV or VEEV.

Thus, this disclosure also comprises a method of formulating a vaccine or antigenic composition that induces immunity to an infection or at least one symptom thereof to a mammal, comprising adding to said formulation an effective dose of VLPs, e.g., alphavirus (e.g., CHIKV or VEEV).

In certain cases, stimulation of immunity with a single dose is preferred, however additional dosages can be also be administered, by the same or different route, to achieve the desired effect. In neonates and infants, for example, multiple administrations may be required to elicit sufficient levels of immunity. Administration can continue at intervals throughout childhood, as necessary to maintain sufficient levels or protection.

Similarly, adults who are particularly susceptible to repeated or serious infections, such as, for example, health care workers, day care workers, family members of young children, the elderly, and individuals with compromised cardiopulmonary function or immune systems may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat, and non-human primates. Most animals are not natural hosts to infectious agents but can still serve in studies of various aspects of the disease. For example, any of the above animals can be dosed with a vaccine candidate, e.g., VLPs of this disclosure, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens. Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this invention.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween-80 emulsion also is contemplated. MF-59, Novasomes®, MHC antigens may also be used.

The VLPs of this disclosure can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the VLPs, or can be administered separately.

Either the protein or an expression vector encoding the protein can be administered to produce an immunostimulatory effect. Thus in one embodiment, this disclosure comprises antigenic and vaccine formulations comprising an adjuvant and/or an immune stimulator.

According to the disclosure, the composition is useful for immunotherapy, treating or preventing cancer or inflammatory disease including liver fibrotic disease; producing an antibody against galectin in a mammal; modulating an immune response in a subject; immunostimulation in a subject; inhibiting an interaction between galectin and galectin receptor; or inhibiting a galectin activity.

Examples of cancers that may be treated by the composition include, but are not limited to, head and neck cancer, lung cancer, non-small cell lung cancer, bone cancer, pancreatic cancer, cutaneous or intraocular malignant melanoma, melanoma, breast cancer, uterine cancer, ovarian cancer, rectal cancer, colon cancer, duodenal cancer, anal cancer, stomach cancer, liver cancer, testicular cancer, fallopian tube cancer, uterine Endometrial and cervical cancer. Vaginal cancer, vulvar cancer, Hodgkin's disease, non-Hodgkin's lymphoma, esophageal cancer, small bowel cancer, endocrine system cancer, thyroid cancer, parathyroid cancer, adrenal cancer, soft tissue sarcoma, urethral cancer. Cancer of the penis, acute myelogenous leukemia, chronic myelogenous leukemia, acute lymphocytic leukemia, chronic lymphocytic leukemia, pediatric solid tumors, lymphocytic lymphoma, bladder cancer, kidney or ureter cancer, prostate cancer, cancer of the renal pelvis. Central nervous system (CNS) neoplasms, primary CNS lymphomas, tumor angiogenesis, spinal axis tumors, brain stem gliomas, pituitary adenomas, Kaposi sarcomas, epidermoid carcinomas, squamous cell carcinomas, T-cell lymphomas, environmentally induced cancers including those from asbestos, and combinations thereof.

Especially, when the at least one galectin antigen is galectin-1 epitope peptide such as Gal-1 epitope peptide #5, #7, #12 or #14 below, especially Gal-1 epitope peptide #5 or #7, the VLP provided by this disclosure may be used for treating or preventing cancer, such as lung cancer, and diseases or conditions caused by HPV infection.

When the at least one galectin antigen is galectin-3 epitope peptide such as Gal-3 epitope peptide #17, #21, #22 or #23 below, especially Gal-3 epitope peptide #17, #21 or #22, the VLP provided by this disclosure may be used for treating or preventing diseases and conditions associated with fibrosis including, but not limited to, lung fibrosis, liver fibrosis including non-alcoholic steatohepatitis (NASH), systemic sclerosis and cardiac fibrosis.

The present application will be described in detail with reference to the following examples, which, however, are not intended to limit the scope of the present application.

Example 1

Preparation of Gal-1 VLPs

Materials and Methods

Galectin-1 (Gal-1) vaccine epitopes were designed by using amino acid sequence and 3D-structure of human and mouse Gal-1 proteins (Table 1). In table 1, epitope peptides #5-#10 are fragments of human gal-1, and epitope peptides #12 and #14 are fragments of mouse gal-1 protein. To present Gal-1 epitope peptides on the surface of protein particle, E3 region of Chikungunya virus (CHIKV) or Venezuelan Equine Encephalitis virus (VEEV) viral structural protein was modified with the Gal-1 epitope peptides. The epitope peptide was fused through linkers SGG (N-terminal) and GGS (C-terminal) between H at 321-position and S at 326-position of SEQ ID NO: 2 for CHIKV, between G at 330-position and S at 335-position of SEQ ID NO: 3 for VEEV.

For the generation of mammalian expression vectors, pCHIKV-Gal-1 or pVEEV Gal-1 plasmid DNA vectors, a synthesized dsDNA fragment of Gal-1 epitope peptide sequence (gBlocks, IDT) was inserted into the specific location of CHIKV E3 envelope protein DNA in pCHIKV or pVEEV vector. pCHIKV or pVEEV vector without any insertion of Gal-1 epitope peptide was used as a control VLP expression vector.

TABLE 1

| Epitope peptide # | Epitope Peptide | Length (A.A.) | SEQ ID No: |
|---|---|---|---|
| Control | None | — | — |
| Gal-1 #5 | SFVLNLGKDSNNLSLHFNPRFNAHGDANT IVSNSKDGGAWGTEQREAVFPFQPGS | 55 | 9 |
| Gal-1 #6 | NNLSLHFNPRFNAHGDANTIVSNSKDG | 27 | 17 |
| Gal-1 #7 | ANLTVKLPDGYEFKFPNRLNLEA | 23 | 10 |
| Gal-1 #8 | ANLTVKLPDGYEFKFPN | 17 | 18 |
| Gal-1 #9 | QPGSVAEVSITFDQANLTVKLPDG | 24 | 19 |
| Gal-1 #10 | ANTIVSNSKDGGAWGTEQREAVF | 23 | 20 |
| Gal-1 #12 | SFVLNLGKDSNNLSLHFNPRFNAHGDANT IVSNTKEDGTWGTEHREPAFPFQPGS | 55 | 11 |
| Gal-1 #14 | ADLTIKLPDGHEFKFPNRLNMEA | 23 | 12 |

FreeStyle 293F cells (Thermo Fisher Scientific, #R790-07) were cultured in suspension with FreeStyle 293 Expression medium (Thermo Fisher Scientific, #12338-018) using a shaking incubator (INFORS HT) in the presence of 8% $CO_2$ at 37° C. 293F cells were transfected with pCHIKV Gal-1 #7, #12 or control plasmid DNA expression vector by PEI (Polyethylenimine, Polysciences, #23966) at the conditions of 0.8 μg DNA/$10^6$ cells, DNA: PEI=1:3, and 1.25× $10^6$ cells/mL culture medium. The culture supernatant was harvested 4 days post-transfection and clarified by centrifugation (3,000 rpm, 10 min) followed by filtration with a 0.45 μm PES membrane filter system (VWR #10040-470). Production of Gal-1 VLP was confirmed by western blot analysis of the filtered culture supernatant without any purification or concentration by using rabbit anti-CHIKV anti-sera (VLP Therapeutics) or mouse anti-VEEV sera (ATCC) and HRP-labeled species specific secondary antibody.

For the purification and concentration of Gal-1 VLP, the VLP-containing culture supernatant was layered onto 1.5 mL of OptiPrep (60% w/v) Iodixanol, Accurate chemical, #AN1114542) and centrifuged at 52,000×g for 1.5 hours in SW-28 rotor (Beckman). After removing supernatant to leave 1.5 mL above the interface, two layers were mixed and centrifuged at 360,000×g for 2.5 hours in NVT100 rotor (Beckman) to form a density gradient. Crude V LPs were collected and purified by size exclusion chromatography using Biologic Duo-Flow FPLC system (Bio-Rad) with HiPrep 16/60 Sephacryl 5-500 HR column (GE, #28-9356-06) and phosphate-buffered saline (PBS).

Fractions containing VLPs were concentrated by Amicon Ultra-15 centrifugal filter units (EMD Millipore, #UFC910024) and filtered through a 0.20 μm PES membrane.

Total protein concentration was measured by BCA Protein Assay (Pierce, #23225) following the manufacturer's instructions. Purity of the VLP sample was confirmed by SDS-PAGE analysis (Any kD Mini-PROTEAN TGX Precast Protein Gel, Bio-Rad, #456-9035) followed by Coomassie dye-based staining using QC Colloidal Coomassie Stain (Bio-Rad, #1610803). Sucrose and EDTA were added to the VLP solution to the final concentration of 250 mM and 5 mM, respectively. Protein concentration of Gal-1 VLP samples were adjusted to 0.4 mg/mL and store at −80° C.

Figure 1:
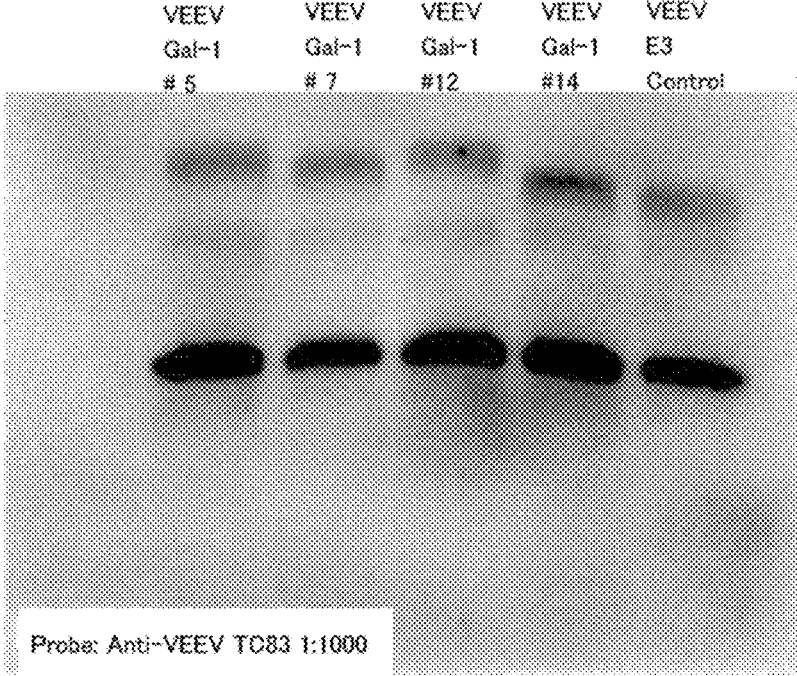
[FIG. 1] Preparation of VEEV Gal-1 VLPs. Each lane is a VEEV VLP bearing Gal-1 epitope peptides #5, #7, #12.

293F cells (10 ml) were transfected with 10 ug of plasmids encoding the indicated Gal-1 epitope into VEEV VLP. The supernatants were harvested and performed western blotting detecting anti-VEEV mouse sera (1:1000 dilution). The expression of VLPs bearing the Gal-1 epitope peptide #5, #7, #12 and #14 in the supernatant were confirmed (FIG. 1)

Example 2

Mouse Immunogenicity Study

Materials and Methods

For the preparation of immunization samples, VLP solution was thawed and mixed with 2% Alhydrogel adjuvant (10 mg/ml aluminum, Brenntag, #250-843261, Batch #5014) at 1:1 (v/v). Mice (8-week-old female, BALB/c, Envigo) were injected with 10 ug (protein) in 0.05 mL intramuscularly into the thigh on Day 1, 4 and 8. To evaluate the effect of peptide-VLP fusion protein on antibody titer against self-antigen, 10 μg of full-length recombinant human or mouse Gal-1 protein (Sino Bioscience) with Alhydrogel adjuvant were injected to mice in two different groups as controls. Blood samples were collected on Day 0 and 15 via submandibular vein and on Day 29 by cardiac puncture. Animal handling, immunization, bleeding, and serum preparation were conducted at Smithers Avanza Toxicology Service (Gaithersburg, MD) following the Guideline of Institutional Animal Care and Use Committee. Whole samples were collected in Serum Separation Tubes (Greiner, #450472) and centrifuged at 1,200×g for 5 min to separate serum. The collected sera were stored at −20 degree until analysis.

ELISA Assay

Gal-1 specific serum antibody titers were determined by indirect ELISA. Immunoassay plate (Thermo Fisher Scientific, Maxisorp, #442404) were coated with 100 μL (500 ng/mL) of recombinant human or mouse Galectin-1 protein (Sino Bioscience, #10290-HNAE and #50100-MNAE) in PBS at 4 degree overnight. After a rinse with TBS-T, wells were blocked with 350 μL of Blocking buffer (5% Skim milk in TBS-T) for 1 hour at room temperature. Wells were washed 3 times with TBS-T. Mouse sera were diluted 1:50 and further diluted serially 1:5 in Blocking buffer to a final dilution 1:781,250. Diluted sera were incubated in the coated wells for 1 hour at room temperature. Wells were washed 5 times with 400 μL of TBS-T and further incubated with HRP-labeled anti-mouse IgG+M+A antibody (Thermo Fisher, #PA1-84388) for 30 min at room temperature. The plate wells were washed 5 times with TBS-T and incubated with 100 μL of HRP substrate (SureBlue TMB 1-Component Microwell Peroxidase Substrate, Sera Care, #5120-0076). Reaction was terminated with 100 µL of Stop solution (1M H₂SO₄) and absorbance of 450 nm was measured by microplate reader (Synergy/HTX, BioTek). Data were analyzed using Microsoft Excel (Microsoft) and GraphPad Prism 8.0 (GraphPad Software). Endpoint titer was defined as the higher serum dilution producing an absorbance measurement higher than the blank plus three standard deviations.

Immunoglobulin class and subclass of anti-Gal-1 antibody in immunized sera were determined by indirect ELISA and subclass specific secondary antibody panel. Immunoassay plates were coated with 100 µL (500 ng/mL) of recombinant mouse Galectin-1 protein (Sino Bioscience, #50100-MNAE) in PBS at 4 degree overnight. After a rinse with TBS-T, wells were blocked with 350 µL of Blocking buffer (5% Skim milk in TBS-T) for 1 hour at room temperature. Wells were washed 3 times with TBS-T. Mouse sera were diluted 1:1000 in Blocking buffer. Each diluted serum was transferred to 8 different Gal-1 coated wells and incubated for 1 hour at room temperature. Wells were washed 5 times with 400 µL of TBS-T and further incubated with HRP-labeled anti-mouse Ig subclass specific antibody Mouse Typer Sub Isotyping Panel (Bio-Rad, #172-2055) for 30 min at room temperature. The plate wells were washed 5 times with TBS-T and incubated with 100 µL of HRP substrate (SureBlue™ TMB 1-Component Microwell Peroxidase Substrate, Sera Care, #5120-0076). Reaction was terminated with 100 µL of Stop solution and absorbance of 450 nm was measured by microplate reader.

Results

By the screening of Gal-1 peptide fragments (as described in Table 1), we have identified two promising Gal-1 vaccine candidates #5 and #7 which induce anti-human Gal-1 antibodies combination with CHIKV virus-like particle platform (FIG. 2A). Immunogenicity of Gal-1 VLP in naïve BALB/c mice was determined by ELISA for mouse and human Gal-1 respectively. Four weeks after first injection, anti-human and mouse Galectin-1 antibody were induced in mice immunized with Gal-1 VLP. For the proof of concept study in mouse models, the peptide sequence of Gal-1 VLP #5 which is derived from human Gal-1 was modified with mouse Gal-1 sequence and obtained Gal-1 VLP #12. There was preference for binding of rhGal-1 by the sera immunized with Gal-1 #5 VLP over binding rmGal-1 (FIG. 2B). On the other hand, the preference for binding of rmGal-1 by the sera immunized with Gal-1 #12 VLP over binding rhGal-1.

For the efficient production of Gal-1 VLP, the origin of VLP was changed from Chikungunya virus (CHIKV) to Venezuelan Equine Encephalitis virus (VEEV). Total 5 different particles including four Gal-1 VEEV VLP (Table 1, #5, #7, #12 and #14) and control VEEV VLP were prepared. Molecular size and purity of Gal-1 VLP and control VLP were analyzed by SDS-PAGE under denatured condition (FIG. 3A). All VLP samples were matched with the theoretical molecular weight and over 90% in purity. Protein bands between 50-75 kDa are fusion protein of Gal-1 peptide and viral structural protein. The molecular weight is varied depends on the length of Gal-1 peptide inserted. Mice were intramuscularly injected with 10 µg Gal-1 VLP protein with aluminum hydroxide adjuvant three times in a week. Four weeks after the immunization, anti-Gal-1 antibody titer specific for human or mouse Gal-1 were determined by ELISA respectively. Four Gal-1 peptides conjugated VLP molecules #5, 7, 12 and 14 induced anti-mouse Gal-1 antibodies in mice but recombinant mouse Gal-1 protein did not (FIG. 3D, E). Gal-1 #5 and #7 are different human Gal-1 epitope sequence peptides and the VLPs bearing those peptides induced anti-human Gal-1 antibodies. Gal-1 VLP #12 and #14 are different mouse Gal-1 epitope peptides and the VLPs bearing those peptides induced anti-mouse Gal-1 antibody efficiently (FIG. 3E). The Gal-1 peptide #5 and #12 encode four β-sheet S3, S4, S5 and S6 near the carbohydrate recognition domain (CRD) (FIG. 3B). The Gal-1 peptide #7 and #14 encodes F4 and F5 β-sheet which might be important in homophilic dimerization (FIG. 3C). The chimeric antigen of self-protein with virus-derived protein displayed on the VLP protein nanoparticles breaks immune tolerance against self-protein and stimulate antibody production efficiently. Though Gal-1 protein is highly conserved between species (FIG. 3F), the sera immunized with Gal-1 epitope peptide from different species induced human or mouse selective anti-Gal-1 antibodies (FIG. 3E). The Gal-1 VLP vaccine could effectively stimulate humoral immune response against self-protein.

Example 3

In Vivo Tumor Model

Materials and Methods

Animal handling, immunization, bleeding, tumor inoculation, tumor measurement and serum preparation were conducted under the supervision of Dr. Judith Varner, Professor of Pathology and Medicine, Moores Cancer Center University of California, San Diego (La Jolla, CA) following the Guideline of Institutional Animal Care and Use Committee. Tumor size was measured twice a week. Tumor volume was calculated as $D \times d2/2$, where D=longest diameter and d=shortest diameter. Mice were sacrificed on day 41 and blood and tumor tissue were collected. Endpoint tumor weight was measured. All the data collected in the study were analyzed by Microsoft Excel and GraphPad Prism.
LLC Model C57BL6 (female, 8 weeks old) mice were immunized with 10 µg CHIKV Gal-1 virus-like particle vaccine with 2% alhydrogel adjuvant at 1:1 (v/v) three times on Day 1, 4 and 8 by intramuscle injection (n=8). Control mice were injected PBS with 2% alhydrogel. On day 15, 200 µl of blood was collected from each animal prior to tumor inoculation. Blood was processed for plasma and stored at −20 degree. Mice were challenged subcutaneously (s.c.) in the flank with Lewis lung carcinoma cells (1×106 cells/100 µL) in serum-free PBS.
MEER HPV Model C57BL6 (female, 8 weeks old) mice were immunized with 10 µg VEEV Gal-1 virus-like particle vaccine with 2% alhydrogel adjuvant at 1:1 (v/v) three times on Day 1, 4 and 8 and weekly after Day 15 by intramuscle injection. Control mice were injected Control VEEV VLP vaccine with 2% alhydrogel. On day 15, 200 µl of blood was collected from each animal prior to tumor inoculation. Blood was processed for plasma and stored at −20 degree. Mice were challenged subcutaneously (s.c.) in the flank with MEER HPV+ cells (1×10⁶ cells/100 µL) in serum-free PBS.

Results

The effect of Gal-1 VLP vaccine on cancer therapy was examined in a mouse model of lung cancer. C57BL6 mice were pre-immunized with control VLP or Gal-1 VLP two-weeks before tumor inoculation. Anti-mouse Gal-1 antibody titer was determined by ELISA. (FIG. 4A). Antibody titers against virus protein were also examined for the reference of immunization (FIG. 4B). Mice received with Gal-1 VLP produced anti-mouse Gal-1 antibody as previously observed in a different mouse strain. The mice immunized with two different Gal-1 VLPs preferentially expressed IgG2a anti-mouse Gal-1 antibodies (FIG. 4C).

Lewis lung carcinoma cells were inoculated subcutaneously on Day 15 and tumor growth was monitored. Though there was no statistically significant difference in tumor volume (FIG. 5A-D) and endpoint tumor weight (FIG. 5E) between control and VLP treated groups, tumor growth in mice treated with Gal-1 #12 was slower than that of other groups.

The effect of Gal-1 vaccine on mouse HPV+ Head and Neck Square Carcinoma Cell model was examined. The tumor growth in mice treated with Gal-1 #14 VLP vaccine was slower than that of control but not statistically significant difference between any groups (FIGS. 6A and 6B).

Example 4

Preparation of VLPs Having Gal-3 Antigens

Materials and Methods

Galectin-3 (Gal-3) epitope peptides were designed by using protein amino acid sequences and 3D-structure of human and mouse Gal-3 proteins (Table 2). For the generation of mammalian expression vectors, pVEEV Gal-3 plasmid DNA vectors, a synthesized dsDNA fragment of Gal-3 epitope peptide sequence (gBlocks, IDT) was inserted into specific location (between G at 330-position and S at 335-position) of DNA encoding VEEV E3 envelope protein in pVEEV vector. pVEEV vector without any insertion of Gal-1 epitope peptide was used as a control VLP expression vector.

FreeStyle 293F cells (Thermo Fisher Scientific, #R790-07) were cultured in suspension with FreeStyle 293 Expression medium (Thermo Fisher Scientific, #12338-018) using shaking incubator with 8% $CO_2$ at 37° C. 293F cells were transfected with pVEEV Gal-3 VLP or control plasmid DNA expression vector to the cells by PEI (Polyethylenimine, Polysciences, #23966) at the conditions of 0.8 µg DNA/$10^6$ cells, DNA: PEI=1:3 (w/w), and 1.25×$10^6$ cells/mL culture medium. The culture supernatant was harvested 4 days post-transfection and clarified by centrifugation (3,000 rpm, 10 min) followed by filtration with a 0.45 µm PES membrane filter system (VWR #10040-470).

The VLP-containing culture supernatant was layered onto 1.5 mL OptiPrep (60% w/v) Iodixanol, Accurate chemical, #AN1114542) and centrifuged at 52,000×g for 1.5 hr in SW-28 rotor (Beckmann). After removing supernatant to leave 1.5 mL above the interface, two layers were mixed to make 50% OptiPrep solution and centrifuged at 360,000×g for 2.5 hrs in NVT100 rotor (Beckman) to form a density gradient.

Crude VLPs were collected and purified by size exclusion chromatography using Biologic Duo-Flow FPLC system (Bio-Rad) with Hiprep 16/60 Sephacryl 5-500 HR column (GE, #28-9356-06) and phosphate-buffered saline (PBS). Fractions containing VLPs were concentrated by Amicon Ultra-15 centrifugal filter units (EMD Millipore, #UFC910024) and filtered through a 0.20 µm PES membrane.

Total protein concentration was measured by BCA Protein Assay (Pierce, #23225) following the manufacturer's instructions. Purity of the VLPs was confirmed by SDS-PAGE analysis (Any kD Mini-PROTEAN TGX Precast Protein Gel, Bio-Rad, #456-9035) followed by Coomassie dye-based staining using QC Colloidal Coomassie Stain (Bio-Rad, #1610803). Sucrose and EDTA were added to the VLP solution at the final concentration of 250 mM and 5 mM, respectively. Protein concentration of VLP samples were adjusted to 0.4 mg/mL and store at –80° C.

TABLE 2

| Epitope peptide # | Epitope Peptide | Length (A.A.) | SEQ ID No: |
|---|---|---|---|
| Control | None | — | — |
| Gal-3 #17 | ADNFSLHDALSGSGNPNPQGWPGAWGNQPA | 30 | 13 |
| Gal-3 #21 | YPGASYPGAYPGQAPPGAYPGQAPPGAYPGAPGA | 34 | 14 |
| Gal-3 #22 | YPGASYPGAYPGQAPPGAYPGQAPPGAYPGAPGAYPGAPAPGVYPGPPSGPGAYPSSGQPSATGAYPATGPYGA | 74 | 15 |
| Gal-3 #23 | ADSFSLNDALAGSGNPNPQGYPGAWGNQPA | 30 | 16 |

Molecular size and purity of VEEV VLPs comprising Gal-3 epitope peptides and a control VEEV VLP were analyzed by SDS-PAGE under denatured condition (FIG. 7). All VLP samples were matched with the theoretical molecular weight and over 90% in purity. Protein bands between 50-75 kDa are fusion protein Gal-3 peptide with VEEV viral structural protein and size variation depends on the length of peptide.

Example 5

Mouse Immunogenicity Study

Materials and Methods

For the preparation of immunization samples, VLP solution was thawed and mixed with Alhydrogel adjuvant (10 mg/ml aluminium, Brenntag, #250-843261, Batch #5014) at 1:1 (v/v). Mice (8-week-old female, BALB/c, Envigo) were injected 10 ug (protein) in 0.05 mL intramuscularly into thigh on Day 1, 4 and 8. Blood samples were collected on Day 0 and 15 via submandibular vein and on Day 29 by cardiac puncture. Animal handling, immunization, bleeding, and serum preparation were conducted at Smithers Avanza Toxicology Service (Gaithersburg, MD) following the Guideline of Institutional Animal Care and Use Committee. Whole blood samples were collected in Serum Separation Tubes (Greiner, #450472) and centrifuged at 1,200×g for 5 min to separate serum. The collected sera were stored at –20 degree until analysis.

ELISA Assay

Gal-3 specific serum antibody titers were determined by indirect ELISA. Immunoassay plate (Thermo Fisher Scientific, Maxisorp, #442404) were coated with 100 uL (500 ng/mL) of recombinant human or mouse Galectin-3 protein (GA3-H5129, AcroBioscience and #599806, Biolegend) in PBS at 4 degree overnight. After a rinse with TBS-T, wells were blocked with 350 µL of Blocking buffer (5% Skim milk in TBS-T) for 1 hour at room temperature. Wells were washed 3 times with TBS-T. Mouse sera were diluted 1:50 and further diluted serially 1:5 in Blocking buffer to a final dilution 1:781,250. Diluted sera were incubated in the coated wells for 1 hr at room temperature. Wells were washed 5 times with 400 µL of TBS-T and further incubated with HRP-labeled anti-mouse IgG+M+A antibody (Thermo Fisher, #PA1-84388) for 30 min at room temperature. The plate wells were washed 5 times with TBS-T and incubated with 100 µL of HRP substrate (SureBlue™ TMB 1-Component Microwell Peroxidase Substrate, Sera Care, #5120-0076). Reaction was terminated with 100 µL of Stop solution and absorbance of 450 nm was measured by microplate reader (Synergy/HTX, BioTek). Data were analyzed using Microsoft Excel (Microsoft) and GraphPad Prism 8.0 (GraphPad Software) Endpoint titer of mouse serum was determined by highest dilution which OD is higher than assay controls+3×SD of controls.

Results

Immunogenicity of Gal-3 VLPs in naïve BALB/c mice were determined by ELISA. Four weeks after the first injection, anti-human and mouse Galectin-3 antibody in the mouse sera immunized with Gal-3 VLP were analyzed using recombinant mouse or human Gal-3 protein. The result is shown in FIG. 8. Gal-3 VLP #17 is consisting of human N-term Gal-3 epitope peptide and induced more anti-human Gal-3 antibodies than anti-mouse Gal-3. In contrast Gal-3 VLP #23 encodes mouse Gal-3 N-term peptide and induced more anti-mouse Gal-3 antibodies than anti-human Gal-3 antibodies. Gal-3 VLP #21 and 22 consisting of human Gal-3 N-term repeat sequence epitope peptide and #22 has longer repeat sequence than that of #21.

Example 6

Flow Cytometry Analysis of Serum Antibody Binding to Cell Surface Gal-3

Materials and Methods 293F cells ($2 \times 10^6$ cells/mL in FreeStyle 293 culture medium) were incubated with recombinant human Galectin-3 (30 µg/mL) at room temperature for 30 min. Cells were spun-down and washed twice with cell culture medium. Pelleted cells were resuspended in FC staining buffer (5% FBS in PBS) and transferred 100 µL to 96-well V-bottom plate. Plate was centrifuged at 800×g to pellet cells and supernatant was discarded. Sera of 5 mice were pooled and diluted with FC staining buffer at 1:250. Diluted sera were added to wells with pelleted cells with and without Gal-3 treatment. Cells were resuspended by pipetting and incubated 1 hour at room temperature. After the incubation cells were down and resuspend in FC staining buffer to wash cells. Repeat washing step twice and resuspend cells in Alexa 488-labeled goat anti-mouse IgG+M antibody (Invitrogen, 1:500 dilution) and incubate for 30 min at room temperature protected from light. Cells were washed twice with FC staining buffer. Cells were resuspend in 200 µL of FC staining buffer and analyzed by Flow cytometer (Attune Acoustic Focusing Flow Cytometer, ThermoFisher)

Results

The recognition and binding of anti-Gal-3 antibodies to the cell surface Gal-3 protein was examined by flow cytometry analysis. Endogenous expression of Gal-3 protein in 293F cell was not detectable by western blotting analysis. Single cell suspension of 293F cells were incubated with recombinant human Gal-3 protein and then washed three times to remove unbound proteins. Gal-3 VLP-immunized sera were diluted with blocking buffer followed by fluorescence-labeled anti-mouse IgG+M. Mouse serum immunized with control VLP were used as a control. Both sera from mouse immunized with Gal-3 #17 and #22 were bound to Gal-3-treated cells. (FIG. 9)

Example 7

Pull-Down Assay

Materials and Methods

20 µL of immunized mouse sera, 20 µg of mouse anti-Gal-3 monoclonal antibody (cl. B2C10, Santa Cruz) or 20 µg of mouse control IgG (Biolegend) were diluted to 1 mL with PBS and incubated with 40 µL of Protein G magnetic beads (GenScript) for 1 hour at room temperature on rotator. Beads are washed three times with PBS on a magnetic rack. Coated magnetic beads were resuspend in 1 mL of recombinant human Gal-3 solution (2 ug/mL) in the presence or absence of 50 mM Lactose and incubated 1 hour at room temperature on rotator. Then, beads were washed three times with PBS and boiled with 50 µL of 1× Laemmli SDS-PAGE sample buffer containing 2-mercaptoethanol. Samples were separated by SDS-PAGE and transferred to a PVDF membrane. Gal-3 protein were probe with anti-Gal-3 monoclonal antibody (cl.Gal397, BioLegend) and HRP-labeled anti-mouse IgG. Membrane was incubated with Clarity Western ECL Substrate (Bio-Rad) and image was captured by ChemiDoc XRS+ imaging system (Bio-Rad).

Results

Neutralization capacity of anti-Gal-3 antibodies induced by Gal-3 VLP vaccine was examined by pull-down assay. Free-moving recombinant Gal-3 protein in solution was captured by anti-Gal-3 antibodies linked to Protein-G magnetic beads. Gal-3 protein was pulled down with monoclonal Gal-3 antibody B2C10 and anti-sera from Gal-3 VLP vaccinated mice but not in Control VLP. Gal-3 VLP effectively induced high-titer anti-Gal-3 antibody which recognized membrane bound and free-moving form of Gal-3 proteins. (FIG. 10)

Example 8

Mouse NASH Model

Materials and Methods

C57BL/6 mice (14-day-pregnant female) were obtained from Japan SLC, Inc. (Japan). All animals used in the study were housed and cared for in accordance with the Japanese Pharmacological Society Guidelines for Animal Use. The animals were maintained in a SPF facility under controlled conditions of temperature (23±2° C.), humidity (45±10%), lighting (12-hour artificial light and dark cycles; light from 8:00 to 20:00) and air exchange. NASH was induced in 25 male mice by a single subcutaneous injection of 200 µg streptozotocin (STZ, Sigma-Aldrich, USA) solution 2 days after birth and feeding with high fat diet (HFD, 57 kcal % fat, Cat #HFD32, CLEA Japan, Inc., Japan) after 4 weeks of age. Gal-3 VLP, control VLP and vehicle were administered intramuscularly (thigh) in a volume of 50 µL/body. An injection leg was changed each time to avoid local inflammation. The viability, clinical signs and behavior were monitored daily. Body weight was recorded before the treatment. Mice were observed for significant clinical signs of toxicity, moribundity and mortality approximately 60 minutes after each administration. The animals were sacrificed at 9 weeks of age by exsanguination through direct cardiac puncture under isoflurane anesthesia (Pfizer Inc.).

For serum samples, non-fasting blood was collected from facial vein in serum separate tubes without anticoagulant on Day 15 (6 weeks of ages). The collected blood was centrifuged at 3,500×g for 5 minutes at 4° C. The 20 µL of supernatant was collected and stored at −80° C. for biochemistry. Serum ALT level were measured by FUJI DRI-CHEM 7000 (Fujifilm Corporation, Japan). For HE staining, sections were cut from paraffin blocks of liver tissue prefixed in Bouin's solution and stained with Lillie-Mayer's Hematoxylin (Muto Pure Chemicals Co., Ltd., Japan) and eosin solution (FUJIFILM Wako Pure Chemical Corporation). Statistical analyses were performed using Bonferroni Multiple Comparison Test on GraphPad Prism 6 (GraphPad Software Inc., USA). P values<0.05 were considered statistically significant. A trend or tendency was assumed when a one-tailed t-test returned P values<0.1. Results were expressed as mean±SD.

Results

Effect of Gal-3 inhibition by Gal-3 VLP vaccine was examined in a mouse STAM non-alcoholic steatohepatitis (NASH) model. Mice treated with STZ and fed high-fat diet develop Non-alcoholic fatty liver disease (NAFLD) and NASH at the age of 6-8 weeks. Mice treated with control or Gal-3 VLP started at 4-weeks-old and three-times in the first week and then weekly up to 8-weeks-old, total six injections.

There was no significant difference in body weight change, endpoint liver and kidney weight observed between any two groups. One mouse in the group 5 found dead on study Date 23, it seemed an accidental death and does not related to the toxicity of treatment. At the study endpoint, serum Alanine Aminotransferase (ALT) level was measured as a general marker for liver damage. The ALT levels in the study rats are higher than that of normal level (17.5-30.2 U/L) (Johnson-Delaney 1996). There was no significant difference in ALT between any groups. To evaluate the effect of Gal-3 vaccine on NASH disease progression, NAFLD Activity score (NAS) was calculated according to the criteria of Kleiner (Kleiner, et al. 2005). There are three different components evaluates for NAS in steatosis, lobular inflammation and hepatocyte ballooning (Table 3, FIGS. 11A-C). H&E staining liver sections from the study in NASH models were scored and analyzed (Table 4). Liver sections from the Vehicle group exhibited micro- and macro-vesicular fat deposition, hepatocellular ballooning and inflammatory cell infiltration. NAS in the Control VLP and Gal-3 #23 VLP groups tended to decrease compared with the Vehicle group (FIG. 11, Table 4. Especially in hepatocyte ballooning score was decrease with VLP vaccine. Though there was no statistically significant difference in total NAS score between any group entered, there was some trend observed in lower ballooning score in groups treated with Control VLP or Gal-3 vaccines.

TABLE 3

Definition of NAS Components

| Item | Score | Extent |
|---|---|---|
| Steatosis | 0 | <5% |
| | 1 | 5-33% |
| | 2 | >33-66% |
| | 3 | >66% |
| Lobular Inflammation | 0 | No foci |
| | 1 | <2 foci/200x |
| | 2 | 2-4 foci/200x |
| | 3 | >4 foci/200x |
| Hepatocyte Ballooning | 0 | None |
| | 1 | Few balloon cells |
| | 2 | Many cells/prominent ballooning |

TABLE 4

| | Score | | | | | | | | | | | |
|---|---|---|---|---|---|---|---|---|---|---|---|---|
| | | Steatosis | | | Lobular Inflammation | | | | Hepatocyte ballooning | | | NAS |
| Group | n | 0 | 1 | 2 | 3 | 0 | 1 | 2 | 3 | 0 | 1 | 2 | mean ± SD |
| Vehicle | 5 | 2 | 3 | — | — | — | — | 2 | 3 | 1 | 2 | 2 | 4.4 ± 0.5 |
| Control VLP | 5 | 1 | 4 | — | — | — | — | 1 | 4 | 4 | 1 | — | 3.8 ± 0.4 |
| Gal-3 VLP#22 | 5 | 4 | — | 1 | — | — | — | — | 5 | 4 | — | 1 | 3.8 ± 1.1 |
| Gal-3 VLP#23 | 5 | 2 | 3 | — | — | — | — | 1 | 4 | 4 | 1 | — | 3.6 ± 0.5 |
| Gal-3 VLP#22 + #23 | 4 | 3 | — | 1 | — | — | — | — | 4 | 3 | — | 1 | 4.0 ± 1.2 |

What is claimed is:

1. A virus like particle comprising an alphavirus viral structural protein and at least one galectin antigen,
   wherein the alphavirus viral structural protein is derived from Chikungunya virus or Venezuelan equine encephalitis virus, and
   wherein the at least one galectin antigen is a peptide fragment of galectin-1 or galectin-3.

2. The virus like particle according to claim 1, wherein the viral structural protein comprises capsid, E1, E2 and E3.

3. The virus like particle according to claim 1, wherein the viral structural protein is derived from Chikungunya virus strain 37997 or strain OPY-1, or Venezuelan equine encephalitis virus strain TC-83.

4. The virus like particle according to claim 1, wherein at least one galectin antigen is inserted into the envelope protein E3.

5. The virus like particle according to claim 3, wherein the at least one galectin antigen is inserted between residues 321 and 326 of SEQ ID NO: 1 or SEQ ID NO: 2, or between residues corresponding to residues 321 and 326 of SEQ ID NO: 1 or SEQ ID NO: 2, or between residues 330 and 335 of SEQ ID NO: 3, or between residues corresponding to residues 330 and 335 of SEQ ID NO: 3.

6. The virus like particle according to claim 1, wherein the at least one galectin antigen is a peptide fragment of galectin-1.

7. The virus like particle according to claim 6, wherein the at least one galectin antigen is selected from the group consisting of:

```
#5:
                                          (SEQ ID NO: 9)
SFVLNLGKDSNNLSLHFNPRFNAHGDANTIVSNSKDGGAWGTEQREAVFP

FQPGS

7:
                                          (SEQ ID NO: 10)
ANLTVKLPDGYEFKFPNRLNLEA

12:
                                          (SEQ ID NO: 11)
SFVLNLGKDSNNLSLHFNPRFNAHGDANTIVSNTKEDGTWGTEHREPAFP

FQPGS,
and

#14:
                                          (SEQ ID NO: 12)
ADLTIKLPDGHEFKFPNRLNMEA.
```

8. The virus like particle according to claim 1, wherein the at least one galectin antigen is a peptide fragment of galectin-3.

9. The virus like particle according to claim 8, wherein the at least one galectin antigen is selected from the group consisting of:

```
#17:
                                          (SEQ ID NO: 13)
ADNFSLHDALSGSGNPNPQGWPGAWGNQPA
```

US 12,636,341 B2

63

-continued

21:

(SEQ ID NO: 14)

YPGASYPGAYPGQAPPGAYPGQAPPGAYPGAPGA

22:

(SEQ ID NO: 15)

YPGASYPGAYPGQAPPGAYPGQAPPGAYPGAPGAYPGAPAPGVYPGPPSG

PGAYPSSGQPSATGAYPATGPYGA,
and

23:

(SEQ ID NO: 16)

ADSFSLNDALAGSGNPNPQGYPGAWGNQPG.

10. An isolated nucleic acid molecule comprising a nucleotide sequence encoding the virus like particle according to claim 1.

11. A vector comprising the nucleic acid molecule according to claim 10, wherein the vector optionally comprises an expression control sequence operably linked to the nucleic acid molecule.

12. A pharmaceutical composition or vaccine composition comprising:

(a) the virus like particle according to claim 1; and (b) a pharmaceutically acceptable carrier.

13. A galectin-targeting immunotherapy method, which comprises administering an effective amount of the virus like particle according to claim 1 to a subject in need thereof.

14. The method according to claim 13, wherein the method is for treating or preventing cancer or inflammatory disease.

15. The method according to claim 14, wherein the cancer is selected from the group consisting of:

head and neck cancer, lung cancer, non-small cell lung cancer, bone cancer, pancreatic cancer, cutaneous or intraocular malignant melanoma, melanoma, breast cancer, uterine cancer, ovarian cancer, rectal cancer, colon cancer, duodenal cancer, anal cancer, stomach cancer, liver cancer, testicular cancer, fallopian tube cancer, uterine Endometrial and cervical cancer, Vaginal cancer, vulvar cancer, Hodgkin's disease, non-Hodgkin's lymphoma, esophageal cancer, small bowel cancer, endocrine system cancer, thyroid cancer, parathyroid cancer, adrenal cancer, soft tissue sarcoma, urethral cancer, Cancer of the penis, acute myelogenous leukemia, chronic myelogenous leukemia, acute lymphocytic leukemia, chronic lymphocytic leukemia, pediatric solid tumors, lymphocytic lymphoma, bladder cancer, kidney or ureter cancer, prostate cancer, cancer of the renal pelvis, Central nervous system (CNS) neoplasms, primary CNS lymphomas, tumor angiogenesis, spinal axis tumors, brain stem gliomas, pituitary adenomas, Kaposi sarcomas, epidermoid carcinomas, squamous cell carcinomas, T-cell lymphomas and environmentally induced cancers including those from asbestos, and combinations thereof.

* * * * *